United States Patent
Ryan

(10) Patent No.: US 8,241,849 B1
(45) Date of Patent: Aug. 14, 2012

(54) ISOLATED GENOMIC POLYNUCLEOTIDE FRAGMENTS THAT ENCODE HUMAN LIPOPROTEIN-ASSOCIATED PHOSPHOLIPASE A2

(75) Inventor: James W Ryan, Augusta, GA (US)

(73) Assignee: Ryogen LLC, Suffern, NY (US)

( * ) Notice: Subject to any disclaimer, the term of this patent is extended or adjusted under 35 U.S.C. 154(b) by 0 days.

(21) Appl. No.: 12/323,364

(22) Filed: Nov. 25, 2008

Related U.S. Application Data

(63) Continuation of application No. 10/161,127, filed on May 30, 2002, now Pat. No. 7,468,266.

(60) Provisional application No. 60/294,404, filed on May 30, 2001.

(51) Int. Cl.
| | | |
|---|---|---|
| *C12Q 1/68* | (2006.01) | |
| *C12Q 1/00* | (2006.01) | |
| *C12N 9/20* | (2006.01) | |
| *C12N 15/00* | (2006.01) | |
| *C12N 1/20* | (2006.01) | |
| *C12P 21/04* | (2006.01) | |
| *C12P 19/34* | (2006.01) | |
| *C07H 21/04* | (2006.01) | |
| *C07H 21/02* | (2006.01) | |

(52) U.S. Cl. ... 435/6.1; 435/198; 435/252.3; 435/320.1; 435/69.1; 435/71.1; 435/91.1; 435/440; 435/4; 536/23.2; 536/23.1

(58) Field of Classification Search .......... None
See application file for complete search history.

(56) References Cited

U.S. PATENT DOCUMENTS

| | | | |
|---|---|---|---|
| 5,532,152 | A | 7/1996 | Cousens |
| 5,605,801 | A | 2/1997 | Cousens |
| 5,641,669 | A | 6/1997 | Cousens |
| 5,656,431 | A | 8/1997 | Cousens |
| 5,698,403 | A | 12/1997 | Cousens |
| 5,847,088 | A | 12/1998 | Cousens |
| 5,968,818 | A | 10/1999 | Gloger |
| 5,977,308 | A | 11/1999 | Cousens |
| 5,981,252 | A | 11/1999 | MacPhee |
| 6,045,794 | A | 4/2000 | Cousens |
| 6,099,836 | A | 8/2000 | Cousens |
| 6,146,625 | A | 11/2000 | Cousens |
| 6,203,790 | B1 | 3/2001 | Cousens |
| 6,900,016 | B1 * | 5/2005 | Venter et al. ............ 435/6 |
| 2001/0021379 | A1 | 9/2001 | Cousens |
| 2003/0072747 | A1 | 4/2003 | Cousens |
| 2005/0100540 | A1 | 5/2005 | Cousens |

FOREIGN PATENT DOCUMENTS

WO WO95/00649 1/1995

OTHER PUBLICATIONS

U.S. Appl. No. 10/161,127 Non-final Rejection Jan. 13, 2005.
U.S. Appl. No. 10/161,127 Non-final Rejection Aug. 10, 2005.
U.S. Appl. No. 10/161,127 Non-final Rejection Jan. 26, 2006.
U.S. Appl. No. 10/161,127 Final Rejection Jul. 26, 2006.
U.S. Appl. No. 10/161,127 Non-final Rejection Apr. 17, 2007.
U.S. Appl. No. 10/161,127 Non-final Rejection Dec. 12, 2007.
U.S. Appl. No. 10/161,127 Notice of Allowance Aug. 8, 2008.
Boyd et al. Biorg. Med. Chem Let. 10: 2557. 2000.
Caslake et al. Atherosclerosis. 150: 413. 2000.
Hiramoto et al. Stroke 28: 2417. 1997.
Ichihara et al. Circulation 98: 1881. 1998.
Kruse et al. Am. J. Hum. Genet. 66: 1522. 2000.
Miwa et al. J. Clin. Invest. 82: 1983. 1988.
Osoegawa et al. Genome Res. 11: 483. 2001.
Sequence Alignment from References (form 892) Jan. 13, 2005.
Sequence Alignment Seq ID No. 1 from References (form 892) Jan. 26, 2006.
Stafforini et al. J. Clin. Invest. 97: 2784. 1996.
Tjoelker et al. Nature 374: 549. 1995.
Tjoelker et al. Biochem Biophys Acta 1488: 102. 2000.
Wu et al. Biochem. J. 375: 351. 2003.
Yamada et al. Biochem Biophys Res Comm. 236: 772. 1997.
Yamada et al. Atherosclerosis 150: 209. 2000.

* cited by examiner

*Primary Examiner* — Yong Pak
(74) *Attorney, Agent, or Firm* — Cheryl H. Agris; Agris & von Natzmer, LLC

(57) ABSTRACT

The invention is directed to isolated genomic polynucleotide fragments that encode human lipoprotein-associated phospholipase A2, vectors and hosts containing the fragment and fragments hybridizing to noncoding regions as well as antisense oligonucleotides to these fragments. The invention is further directed to methods of using these fragments to obtain human lipoprotein-associated phospholipase A2 and to diagnose, treat, prevent and/or ameliorate a pathological disorder.

6 Claims, No Drawings

```
                              SEQUENCE LISTING

<160> NUMBER OF SEQ ID NOS: 2

<210> SEQ ID NO 1
<211> LENGTH: 441
<212> TYPE: PRT
<213> ORGANISM: Homo sapiens

<400> SEQUENCE: 1

Met Val Pro Pro Lys Leu His Val Leu Phe Cys Leu Cys Gly Cys Leu
1               5                   10                  15

Ala Val Val Tyr Pro Phe Asp Trp Gln Tyr Ile Asn Pro Val Ala His
            20                  25                  30

Met Lys Ser Ser Ala Trp Val Asn Lys Ile Gln Val Leu Met Ala Ala
        35                  40                  45

Ala Ser Phe Gly Gln Thr Lys Ile Pro Arg Gly Asn Gly Pro Tyr Ser
    50                  55                  60

Val Gly Cys Thr Asp Leu Met Phe Asp His Thr Asn Lys Gly Thr Phe
65                  70                  75                  80

Leu Arg Leu Tyr Tyr Pro Ser Gln Asp Asn Asp Arg Leu Asp Thr Leu
                85                  90                  95

Trp Ile Pro Asn Lys Glu Tyr Phe Trp Gly Leu Ser Lys Phe Leu Gly
            100                 105                 110

Thr His Trp Leu Met Gly Asn Ile Leu Arg Leu Leu Phe Gly Ser Met
        115                 120                 125

Thr Thr Pro Ala Asn Trp Asn Ser Pro Leu Arg Pro Gly Glu Lys Tyr
    130                 135                 140

Pro Leu Val Val Phe Ser His Gly Leu Gly Ala Phe Arg Thr Leu Tyr
145                 150                 155                 160

Ser Ala Ile Gly Ile Asp Leu Ala Ser His Gly Phe Ile Val Ala Ala
                165                 170                 175

Val Glu His Arg Asp Arg Ser Ala Ser Ala Thr Tyr Tyr Phe Lys Asp
            180                 185                 190

Gln Ser Ala Ala Glu Ile Gly Asp Lys Ser Trp Leu Tyr Leu Arg Thr
        195                 200                 205

Leu Lys Gln Glu Glu Thr His Ile Arg Asn Glu Gln Val Arg Gln
    210                 215                 220

Arg Ala Lys Glu Cys Ser Gln Ala Leu Ser Leu Ile Leu Asp Ile Asp
225                 230                 235                 240

His Gly Lys Pro Val Lys Asn Ala Leu Asp Leu Lys Phe Asp Met Glu
                245                 250                 255

Gln Leu Lys Asp Ser Ile Asp Arg Glu Lys Ile Ala Val Ile Gly His
            260                 265                 270

Ser Phe Gly Gly Ala Thr Val Ile Gln Thr Leu Ser Glu Asp Gln Arg
        275                 280                 285

Phe Arg Cys Gly Ile Ala Leu Asp Ala Trp Met Phe Pro Leu Gly Asp
    290                 295                 300

Glu Val Tyr Ser Arg Ile Pro Gln Pro Leu Phe Phe Ile Asn Ser Glu
305                 310                 315                 320

Tyr Phe Gln Tyr Pro Ala Asn Ile Ile Lys Met Lys Lys Cys Tyr Ser
                325                 330                 335
```

```
Pro Asp Lys Glu Arg Lys Met Ile Thr Ile Arg Gly Ser Val His Gln
            340                 345                 350

Asn Phe Ala Asp Phe Thr Phe Ala Thr Gly Lys Ile Ile Gly His Met
                355                 360                 365

Leu Lys Leu Lys Gly Asp Ile Asp Ser Asn Val Ala Ile Asp Leu Ser
370                 375                 380

Asn Lys Ala Ser Leu Ala Phe Leu Gln Lys His Leu Gly Leu His Lys
385                 390                 395                 400

Asp Phe Asp Gln Trp Asp Cys Leu Ile Glu Gly Asp Asp Glu Asn Leu
                405                 410                 415

Ile Pro Gly Thr Asn Ile Asn Thr Thr Asn Gln His Ile Met Leu Gln
                420                 425                 430

Asn Ser Ser Gly Ile Glu Lys Tyr Asn
            435                 440

<210> SEQ ID NO 2
<211> LENGTH: 42611
<212> TYPE: DNA
<213> ORGANISM: Homo sapiens

<400> SEQUENCE: 2
cttttctttt ttttctctct ctctctcttt ctttcgttcc ttctttcttt cttttgaggc      60
ggagtctcat tttgtcgcca ggctggagtg cagaggcgcg atctcgactc actgcaacct     120
ctgtctcccg ggttcaagca attcctgcc tcaacttcc cgagtagctg ggactgctgg       180
cgtgccgtat cacgctcggc taatttttt gaattttag tagagacggg gtttcgctgt       240
gttcgccaca atggtctcga tctcctgacc tcgtgattcg cccgcctccg cctcccaaaa     300
tgctgggatt acaggcatga gccaccgcgc ccgccccgga gttttcttat ctgtagatct     360
cctacaggga caatctctct ctccgtctct ctctctctct ctctctctct ctctctctct     420
ctctctctct ctctctctct ctctcacaca cacacacacc actacacacc tctcactctg     480
cctcctctct ctctctccct ccgctctctc tctcacacac ccttctccct ctctccctct     540
ctctcactct ccctttgagg agtattgcgt ttttggagcc cagttatgcg tggctgctgt     600
aagaacaaaa caaagcactc tttgtcctac ctggagcatc ccctgccgg ccagataaga      660
tcacagctgt gtcaccaagt caagggagag gctcatttt aaaaaattaa gcaaaatcag      720
aaaacagaga acactgtctt cctcatcatc tcctggagct tgtaagagaa atttctgtca     780
ccaaaaacga aaagttcggg cttttattca tgcctgtggt tcttgggatt actgcagtgg     840
tgatgaggaa ggagaggtgc gtatggctca taaatggcag cttgccacct ttaaaaggca     900
cacggattca gatttgggat gtgttaacaa atcaggcttg cacaaattac ttttgatcca     960
aatgagaatg ctgagctggg agactggtat atgggtagga gctggaaaat gtatccctg    1020
aggtgttggc aatcccaaga ggctcagcac gaaaccttga gcttacattg aattcagaga    1080
tctgagcatt aagcactggc ctgatcaaga agaagcagat ggccttctgg tcacgaggca    1140
ctggtgagcc tccatcaccc aggcagattc cctcacagag gaattctgct ggccctgcag    1200
aaagtggtga cacagcgcac caccttggca ttttccagca ggcctacttc agctccttgc    1260
acttgggcac tgaaagtgct ttcccctccc cagatatttg tgcaccagaa gctgctgctg    1320
gccatgtggt gatgtctcaa tgtctttctt cattgaactg ggcccttcat acccaaggct    1380
ggcaccatag tctgtgactg cctactgtac agccagcaag actgaaggag ttgcagcatt    1440
aggagtgttg tgaatctggt tcagccactc attttacagt tgagaaatcc cttctgaggt    1500
```

```
gtggaagggc ttgcttagca ccgcaggact tttccctcag acagaacctg ggacagctgg      1560
gtcctcattt cctctccatt gtgtctctgt cccctttgca cttttgttgt gaggaacata      1620
catgggccta aacacattcc ctcactctca cctttgcaca tgaatatgac ttaccacact      1680
ctttgaagct ctgtcagcac agaacattaa gaaaagtgct aactgggtac ctgagcagct      1740
ggagtgggag ccctgggaa agtcagttta ggagtcccct ttatcttcct tttcctgata       1800
cccaagaaga tggctatttc ctggaaagga aggtggatat tggattattt acactctgat      1860
tcctcttaag cctaattttt tttcaagatt cgtgataata agcctgactg acgtctcaag      1920
atgttgagaa atttccataa aataaaagca ttgaagagaa agtactgagt gaagggaaat      1980
tgaagagaaa cattcagttc taaaattgta ttgtttcaga atatgattct gggttcttac      2040
tgactttctt catgacgcca gccacctgtt agacacatta tgtgccctca ctgtcatttt      2100
gctcaatttt atgggcgtga ctcaacacta acagaaacag gctaatacat acaaacatgt      2160 aggttttgg tttttaaaga aacttagcag ttgaggagaa ataaaaagtc tattgtaaga      2220
gtagatgctc attgaattaa gtgggctagt tgattcctag tagaacttgt attcattcat      2280
tcattcactt caaaaaatat ttattgatca gatcctaagt gccaggtact gagtacagca      2340
cagttagtaa gatagatatg ctctctgctc tcacagtgct cacattctag aattgaggga      2400
tgaacagggt gaattcatat aatgagaaga aaagcaagca gattgctgca gtatagtggt      2460
gtgtgtgtgt gtgtgtgtgt gtgtgtgtgt gtatgtgtgt gttggatata tgggagggc      2520 ctagcttctt ggattggatt gtgaggagag acttctctgc aagaaggcct ggagatgaaa      2580
cctcaggaag atgggcagac gtccctgcag agggaaccac aagcacaaat gtcctgctcc      2640
tgggaacagg tgtgatgtgt tggaggcaca gttggaatgc cagtgtggct ggagttaggt      2700
gagggagaag gagagttgga ggagtgagct ttaggggcag gagccaggtc aggaagaccc      2760
tcataggcca agggaaacat ttggatttta ctctttacaa tgagagaagc caaaagagag      2820
tttgaagcag agatgtgaca taattgattt acttttataaa gagatgactc tgggtgctat      2880
gtggagaatg gattacaggg gaaggagagg ggacagaaga aggccagaag cgagtttact      2940
gatggggggt ggtagcagta gatgggcgta ggctattttt tggagttaca gtgggaagtt      3000
aatgtttctc tgtctcgaat ttcccatcta caaaatggga atgagattgc tatacctggt      3060
ccacttgtaa aaactaataa acaaatgaat atgccctgaa gcataatgta agacattatt      3120
accattatta tttgctcata ttgtattact ttgaattccc tgtgctttat cttaaaattt      3180 atttaataa atttgatgtc ttattatatt attttcagta aacctaattt attatacata       3240
aaagtatctt tctctgttcg gagaactgga aactcttaac taagagttac caataaaaac      3300
aagtcgtcac aaaatgcagg gaaattattg ctaaaataat agctggctta atttcaaaag      3360
ttgaatatgg tcagataaaa attcaaaaat agaataatta aagctgggaa tgggaaaaaa      3420
atattttgga cagatttgcc tttgtcctgg ctgtggtcat gcagatatct gtgagtgcaa      3480
agatttgtag ataactgaaa atatctatat ggcagcagaa tttctggaga agtctgtgga      3540
ccagagttgg gtagggttgt ttcccttagt gaagcattct ctctcagagg aagctcttga      3600
attttctctc gtttatcact aagtttaga gtgtcaggaa gttttaaagt tgtttaccaa       3660
ctaggatagt gacgttcttc gcagagacag gacaagtaac tgccacaata aggcaactct      3720
atttctcttt cctgactcac tctgatgtgc aagttactag aaggagatat gcctgcttag      3780
aggaaaaaaa gctcttcctc atttgtattg tgggcagcag aaatgtcagc tcgtgactta      3840
atagtcccta ggtcatgtta acttgccaga tcccttaat tatttattgg tcagtgtgtc      3900
```

```
tgaatttcag cttgaagtgg ctagtctggt gattcaaatt gcagacaaaa tgtgatagta    3960
attctgggat ctgtatgatt tatctcttgc catatcaacc accatatttt tcttagggct    4020
ggagagtggg ggtgtttggg tatcttaaag ggagaggtta catctctcct tgaagccaga    4080
aatctatttg ttttcactca cgttttgaaag gttgaattag ttgctccttt aaaaatcagt    4140
ggatattaca tacaaatgta attttccagt ttttcttgga agcaatcaga tgatctagtg    4200
acatggagct gccattccta catggaagca attaactgga atagagtggt agttgccttc    4260
tttggatggt ccagtttgca ccatccaaat agaataagga cagttcacgc cagtccttat    4320
tctattgcat gaacctgttt gattcattta aattacctgt ctggcccttg tagacttttg    4380
atttttaact tcaggtttag ggcaatcaag tgtaacctgt ctgttatact ttcaccttca    4440
tgtaatgcag gaatctatat tccagtatcc ctgctggtag tccccaaacc tgtactttaa    4500
ctgctcctct gataaagaag ataatgctaa ttgttgaaaa gctactgttg atggagctgt    4560
acagtctggg cctacataga acatgtttag gaactttgca caggactgtg gctgtcacat    4620
gcaacctagg ttttccacat taaaagtaaa cattcctcat tccttcaaca gctcctcatg    4680
tgacttgctg ccttgttccc tcatcattct ggttattttt gggttactgt cccttgtcct    4740
gaacctttat ttgttaaaat ccttaaatcc ccaccaattc aataagatgt ggtctaactg    4800
gtgcagaatg cagtgggagg gtggcctccc tttctctatg atgtcatact tttgtcatgc    4860
aactgaagat gtctttagat ttttcctggc ctatccattg tgttttaaa tttactttca    4920
gggcttattt tccagttaga ttgttcctga gagtttacag gagaactgct caatgtacag    4980
cttgagagca atggttttca gctgaggatg atttatgccc ccactccagg ggacatctgg    5040
caatgtctgg agacgtaata tttagttgcc acaactgggg tgtgctattg gcatctagtg    5100
ggtagaggcc agggatgttg ctaaacaccc tgcaatgcac aggacagccc ccacagccaa    5160
gacttatcag cccctagtgt cagcagtgct gagcttaaga attcctactt tagggtccgg    5220
gtctaggttc agatcctggt ttagctactt cctatccttg tgaacttggg cacgttattt    5280
aacctctttg tcttcattat ctcaactgta tgtcaaagaa ctctgaggac taaatgagtt    5340
catttatatg aaatgcttag aagggtaact gtatgtacaa acactatctt attttttctac    5400
catattttat tcattttggt gtgtacatat gacatcagat aagtgggtgg gtaaagtttg    5460
agggatagca cttcatttct aatcttgcct atgggatggg cactagtgca tttggatgtt    5520
ttagggagct aacagctttt ctcagaaatg ccttctctct atggtcccca ttatcatttt    5580
tccggcttct tttagtattt tcctccatat tggggcatat atgtcagttt aatactgcat    5640
cctcctggag aatatggaca ctgagttcct ttagcgggag agcatctgtg cctgttgctt    5700
gtacatccca tttccggtgt gccccaggct cctccacacc ccagtcaccg tggcttgcac    5760
ctgcacaaca gattcctggg gctgtgtagc aattggtaga cttggataa taataatagc    5820
atttctccaa gggctcacat ccccataaga accccattat cagggttcct ctttgacaga    5880
tgaggagaga aaagcagaaa gtaggtaaga acttaactga agtcaccaaa ctagtaagta    5940
gcagattcaa gattcaaacc ttggcagcca gaaactggag ctaaatttct aaaccacttt    6000
attactctga tacaggtaag ttttctcaag aagtataccc atgaccttaa cctaaccatc    6060
atgtagccat ttatgcatac aacactcaac agatccagtt actcttactc ttactattgt    6120
gagtaatata gttggggggac tgagtctgag agtaagatca ggaacttaca gtatagcagc    6180
aggctgccca ttgatcttag acaacttttta ccttttatga cctttaagcc atatagaaca    6240
ccaaacattt ggacatttgc acatgggatg cagattaatt cccatttcca aaattgtgag    6300
```

```
tagaatcaac taattatatg ttacttgcag gttttgcatc tcatgcatct gcctccctag   6360
aatgaaataa aatttcttcc ttattaaaca aggatagagt tgccccagct tttcttagac   6420
cagggtttct caacctcagc agtattgaca ttttgagatt cctctatgtg tagggctgtc   6480
ctgtgcacta cagatgctta acagcatccc ctgactgcta ctcactagat gccagtagca   6540 gcccctcct ggttgtgcaa cgcaaaaata tctccagaca ttaataagtg tcttcttggg    6600
ggccaaaaat gccttagttg agagacactg ctgtagagtg atgttctagc tgcattctcc   6660
agccttcatc ctattgtaaa atatccaaag aagatttat cttcttcagc aatcatttgg    6720
tgtggtaatg ggtcagtttt gaggtattta agccactttc tttgacttta gttgaaactg   6780
aattgggcta ttatttgctt tttgtctcat tcagttactt tatatgctcc atattagttt   6840
tctattgctg ctgtaaaaat tttctacaaa tttagtcact taaagcaaca taatttatta   6900
tctcatggtt ctgaaagtca gaagtctgac atggccttac taggctaaaa taacaggttc   6960
agtgaacctt cagaggtcag ctagtctgtg ttgcttttcct gaggctctag agagaatctg   7020
tctccttacc tttccaagat tctagaggcc atccacatgt tatagctcat gcccgcttcc   7080
ttcattttca aaaccagcca tggtgggttg agttctcaca tcacatcatt cagatctctt   7140
cttctgccat cctcttatac ttttaaggac tcttgtgatt acattgggtc agataatcca   7200
tgataatctc cctatttaa ggtcaactga ttaacattaa ttccatttgc atcttaattc     7260 tttttgcca tggaacatta catattcaca tgttctgggg tttagaatat ggacatttgg    7320
gtgggagtgc attattcaac ctgccacatg ccccattcc aaaggtcaat caggaagaat     7380
ttggaaagag agtactgata cttaacaaat gagcattttc ttttctgact ctttactaat   7440
aacacaagag ctaaggccca cctgccctaa tctcttgcca ggactgggtt ttacttggat   7500
ggtttatctg tcagctttc acagagattt caaactcgag attggacatt ttatctattg    7560
ttttgggttg tcttttgttt cgaaaaggga aatgatgcct gatgagaatt taacagtgac   7620
aaatagggga aatcgggatt tgtggcagtt atggttgtgt atggagacta caactgagat   7680
ctgaagaaca ggtagggcac tgtggttca gtgggagaaa tgaagtctgc aggagagagg    7740
cagaaaggta gaatccgttt aaatggaatg tattatctga gtgctcattg aaagtcttct   7800
tgattgccag gatgatattt tatctagtgg tcaaggggcc aaattgaaga tagttatttt   7860
caggccttac tatttgaaga aaatcattga tttttaaagt gaacattccc attgatttag   7920
aatgttggtg gctcatgcct gtaatcccag cactttgaga ggtagaggtg agcggatcac   7980
atgaggtcag gagttcataa gcagcctggc caacatggag aaaccttgtc tctactaaaa   8040
atacaaaaat tagccaggca ttatggtggg tgcctgtaat cccagctact cagaaggctg   8100
aggcaggaga atcacttgaa cctggaaggc ggaggttgca gtgagctgag gtggtgctat   8160
tgcattccta ggtgacagag tgagactcca tctccaaaaa aaaaagttt gtgttttgt     8220 attgaccagt gattggggtt atggtaatag attttcatac aatatgatga tgaagacggc   8280
tgtatcaagg gttttagtgt agtcctgttg gattctctag ttctaagaga atgtctaaag   8340
ttaccattaa gttttcagg gtcctagttc ttaaatataa atacatttct agctaactca    8400
tatcccatgg ttgagaaaaa ggcacttatc tgtgtaaaga gaactttaaa agttaaaaga   8460
cttcttatga attattcctg tgtgttcata ttcagaagcc tctgtggtca ttgtgattat   8520
tacatgttaa tatggttcct ggctcataac tcccgttgcc cttgctacag tctttggtta   8580
taatattgga gtgctttaga ccccagaagc aggtctcaga aagcagaatc tttctctctg   8640 acctttcct gccttccttt ctactgccca aggcaggact ctaatctgat tgtaggttat    8700
```

-continued

```
aagacccttta ttcagggaag ggtcctctta ccttggaaaa aggaatgctg cacagacaga    8760
ccaagaagaa tctgaataga cagggcttgc tgggttgccc ctctgagtct attagcatta    8820
gagcttaccc ttactgtcca gtcatatttc tacacagctg ttcatacttt gttgaaccta    8880
tgcataaaaa tagacagttt cccctgtatc tttgggtctt cattctgaag gctccttgtg    8940
aatacacatt aaataaataa tctgcctttt acaagttgat ttttcagtga cccttcagag    9000
gtccaagggg aatgccaccc gtggcccect tggccccttc agtgtgcatg tattcgagcc    9060
tagaaatgcc tctggaaaaa aatctgttag caagtcatta tttgcgaaga gataactcaa    9120
tttacctttt tctgttatgt ttggatttt gaaatcatgt attaacttta taatataatt    9180
aaatgtaata ctgaaataag atcaaataaa atcaaccaaa attataaata atcttaaaga    9240
gttgcacata tataccttt ttttctgatc aaaagaaaga tgttgaataa ggaaatacag    9300
tccctctgca agtagtttaa gaagttttgg ctggacacgg cggctgatga ctgtaatccc    9360
agcactttgg gaggccaagg tgggcagatc atgaggtcag gagatcaaga ccatcctggc    9420
caacatggtg aaaccccatc tctactaaaa atacaaaaat tagccgggca tggaggtggg    9480
cacctatagt cccagctact cgagaggctg aggcaggaga attgcctgaa cccaggaggc    9540
agaggttgca atgagccgag atcacactac tgcattccag cctgggtgac agagtaaaac    9600
tctgtcaaag aaaaaaaaaa atttagagct ccagcaacac atttaccagc tgcctatctg    9660
ggtctttcta gcctgtacaa taggagctgc ccttacacga aagccccatc tctttgaaat    9720
ctttctgtct acattcctgt tgctctcaga acttgtacca tatcatctaa gaattataaa    9780
atgcccctgt aatttgcttt cttcctgtat tatattgtta atatatgcta gtcttgtctc    9840
tgaaacacaa ttgtaaactc tctgagagta gggattgtgt caaattctct ggtacttacc    9900
acagttgttg ccataggaga gggcatatag tatttgctta agaaatacccc tttgattgaa    9960
tgactgcaga tctgataatc aggataggcc atgctgtgct ccattaaggc aataacagct   10020
tcacctggaa atttcagtgg cttaacacag caaaggttta tttcccattt gtgaaaggtc   10080
atttgaattg gcaggggctc ttctctgttc agtgactagg tatccaggcg tctttcactt   10140
caagactgca ctacatcagc acatgatttc taagtttgct gtgtcaggga aaggaaggca   10200
tgaaggagat acagtgactc tgttgcagac gacttctgtt caaattttg tttctcagga   10260
attagcccca tgggcccagc ccaaccacag gggcggctaa gaaatgtagg gaagcacata   10320
gatgttcagg agcactcatt gtctgtgcca cacatctata ttacatcttc ccgcaaaata   10380
gctatactaa cgagtgcttc attagtgtca gtgggacacc ggatcattaa acttggctcg   10440
gtttgtatta gtaaccagat gtgctagatt tattcactca gcaggcattt actgagtgcc   10500
tctgtacacc aggcactatt ctaggtcttg ggaatacagc aggggaaaa accatcaaaa   10560
atccttacac tcacagaact aagtttttag tggaaggtga taaacaacta acaaataaca   10620
tacaaggtac gttagttggt gataaatatt ggagaaaaat aaagtaggga gggaaatagg   10680
gaatgtattg gtgtgaagaa ggaggttaga ttgcaatttt aaatagattg aaccgggaaa   10740
gtgtcactga gaaagtatca ctggagcaaa aacccggagg tgagaggacc agtcatttgg   10800
gtgtcagagc aaagagcatt cccataaaag ggaacacatt caaagccctc aaagtgggga   10860
tggaaggtgg gtgtggagta cttggcatgt ttggtgaatg gcaaagaagc aagtgtgatt   10920
gcagcaggtg tccaagaggg gctagggaa ggattgggag tgtgttgagt aaaggttatg   10980
tagatcatta taagctattt tgggtgaatg gcttctcccc cgtaacatat aacaccattt   11040
gggggttttg tgcagaaggg tgacacaatc actctggctg ctgtgtttggg gatagatttt   11100
```

```
agggtcaagg gcaaaagcag ggagactcgt tagaggtgat ggcaaatttt aggtaagaga    11160
tgatggtggc ttggaccttt tctatccccc acaaaagttg aagggccaaa ttttaggggg    11220
gaaaatggat gcacaaatgc aagatagttt ttgctaataa gatgttagca tacagactaa    11280
ttataattta ttattaccac acatctcata ttctcttgtt tcatttactg attcaacaag    11340
catctatgca atactacttc ttccaggccc tctattaggc actgagacaa caaataagac    11400
ctgacttctg cttttggaa acttatatca tagtaggatt atagaaatta gcaagaatat    11460
aacatcatat taacacccaa acaaccaca gcagcagaaa tatagtcact atataattaa     11520
atgatggaaa tagccaaaat ttatgaatta tttactatgt gctagacata cctatggata    11580
ttattatgat gatgacagat ggttgttata tttgttatat tttgttggct atttttatag    11640
ctgaccatac tgttataaag ttagaaaact agtgaccaaa aacttaatct aactgtctga    11700
aagtattatt tctctgctct acaatccaat gtaatcctta gtaatgtagg taatggtaat    11760
cctacattac caaggatttt accattgtag taccaatcta aaccccagca cagaaaatac    11820
atgttttatt ttttccaagt gttactagta cctcagcctt tcttgatttg tcagcttatt    11880
taaggcctct tcattgcata cttcttttt cttttaatca tctgcttcga aggagactaa     11940
gctgaaactg ctgctcagct cccaagatgg tgccacccaa attgcatgtg cttttctgcc    12000
tctgcggctg cctggctgtg gtttatcctt ttgactggca atacataaat cctgttgccc    12060
atatgaaatc atcaggtaag aggtgtattt gttcaaggtc ttgagcaact gatctgtcgc    12120
catacttcaa gtgggcccca agaagttgca catctgcaca tctaaacaag tcctatttaa    12180
aggcttatgg agatcctgta ttctcctgga gtaggggaga ggttctcact ttttcctcat    12240
ttcaactgaa attgaagaag cacttgtgtt cttcagtatc aggactgcag gacagaacca    12300
ggatgggaca ttttaagata tactggacgc tcagcttgca atcaccacgg agaacctcct    12360
taatgccacc ccttctctct ctgactgccc taacgcatgc ccacacaagc atagtaatgc    12420
aactggtctg gagtccactc caagacagcc tcaaaacctg cttccatgag gtgaaaaaga    12480
agcaggtgtc ttgttcaaca ggcatactcc tggttaatag tggaaagtca tgtgagataa    12540
caatttcagg tcttgggatc caaaaggaaa caatctttcc tacctgataa tagagagaag    12600
tagggacaag taggtgctag ggagttccag atgagaatgg atgtgatcac tcattctttc    12660
ttgccttgtg gtaagtgggg aaagaaagag gtggaaggca tagactaaac ccaggaggag    12720
tggccaaaac gggacagcca tcttagacg gctacattta atgtcactaa gagagacctt     12780
aattggaaaa agattgtttc tggagctttg caaattcctg ctcatcccag aggattgtga    12840
tgcataaact tctcttttcca gtctcctatg gagagcagtg taggtggctt ctgaatggtg    12900
tcatactgac tataccctaca gagctgtgca cctggatagt tgtgggtcac tctggatcta    12960
attgttcaag cttgatgggt gactccttac gatagcattt gcaaagagc tttcataatt      13020 cagtaccta aattttgccc tactacataa gcaggaaaat gaatgcatta ggagaggttt     13080
tatatcttat atctacattt gcataggaaa tagaataata tctcacaggt ccattcatcc    13140
tataacgcat caggaagtta agtcatcaag gatacactgg tgactaagac aataaatgtg    13200
tagtcaaatt caagggtcct gcatcctaga tgacattaag ttcattttc ctactacctt     13260 tttcatggat tgagaacagg taatatctta gatggtggga aaatcatcat tcggaaaca     13320 tttatatcct tcacttttaa ttggtacagg gtaaaaattt aaacattttt aaaatccctt    13380
tgtctttaaa aataattgga aggctgttgc tggactgaca gaaacttgag gacagggacg    13440
ttgctttatc tttatagtcc cagcattgag cccaatgcaa tgcccattct aaatgttcaa    13500
```

```
aaatgaatgc aggccgggca tggtggctcg tgcctgtaat ctgagcactt tgggaggccg   13560
aggtgggtgg atcacttgag gtcaggagtt cgagaccagc ctggccaaca tggtgaaacc   13620
ccgtctatat taaaaaaaaa aatacataaa attagctggg tgtggtggtg cacacctgta   13680
gtcctagcta cttgggagac tgaggcagga gaattgcttg aacccagaag aaggaggttg   13740
cagtaagctg agattgcacc actgcactcc agcctgggct acagagcgag actctgtctc   13800
aaaacaaaca aaaaagaat gcatatatat tggtttaaag tattagaaac agtttattaa    13860
ataagattaa aataataggt gattctttat aatttcttac taaatgaata cacagaaaat   13920
atggctatgc aggttaaaag gtttgtagga atgggctaga gatatcctct ttactaatgg   13980
aggacataaa gccatataag agtgtaattg tcctagcatg tatacagttc atctccaaac   14040
ccaagactga acatcaggaa tatttgacaa atgaaaacca ccaaaaatat gtaataaaat   14100
taatagcatg ccataggttc caatcctcct attaaaataa agttgaagaa aactaagaag   14160
agacatttat aaattctgaa ccacaaaact gtgtgagtgg tcatttgatc tgatgagtct   14220
cctccttcca cttccttaat gatgactcct gacagatggt tagagaatgg gaaatccagg   14280
cccataaccg ggtcagctgt aggctatgga gcctgttcca cagccacccc caggcaccct   14340
ggcactggtg cataggaccc catagaccta taccaaaacc tggatcagcc tgatgattcc   14400
tgaggtcttc tcagaggtca ggtgtcctgg aacaggcaga cctcaccttg acctgaatgc   14460
tcctgaatgc tgagtgagga aacttcccag ggagaacagg tgttggacaa ccagggcact   14520
cctaacttat tggaaaatgt tcccctgtcc tttggaattg agatctcaca agcggaggct   14580
tgtgtttggg tgaaaccctc ccatgcctcc agaactgagc ctccaattct agaggtagtg   14640
tctccaacag cagctgtggc cctggggctc cttagcgagt tgtgtgagcc agaggtctcc   14700
ctgcagcaag ccctgcacag gcacaccatg cctgcctagg ggtggggttg cagtagcacc   14760
aggctgctta ccacagaaga agaagcaggt gtccctacct taaggtcctc ctccttggga   14820
cttcacatct ccctgttaca ccagaagcat ggctcagtag atactctttt aatgaagaa    14880 gagccttttg taattcaaaa tagaccctga aagttcacct tgcaggtaaa gtttaaaaaa   14940
aaagtttctg gggtttgaat ctacctgggg agaggttaga cctgctaaaa cttccctaag   15000
gactcagcac agatttacct agcaagagta aatggactct ggggaaggag taaacagcat   15060
tatttgtcta ccccttatgt gtcatgtttt gtactaagaa cttgacctac attctcacct   15120
catctttaca actgtactgt gggctggtca agtgcttttg tgtcattta cgaatgtgga    15180 tcagagaggg gagcaactag gccagaggat tatagcttgt aagaggtaca cctgaaatct   15240
gaaatagaac catgtccctc caattcacag ggtttgttca tctccatccc ctctcccctt   15300
gcctttcttg aaactacctc ctaccatttg accatggatt gctgacctgt gtgtcaggca   15360
ggtggtctgg aacttcagcc cagtgtctct taaactttaa tgggcactcc ttttctgatt   15420
gagtggaatt gtggtgaagt ccaggagcct gcatttccaa gctccagctg gtgccagtga   15480
tgctggtcca tggatcagct ttgagtagct gagccttatg tattgaaagg cttcatcatg   15540
ggcaggtgtt tcacacatga gtcaccagtg tggaggctgt aaattggttt cttcccatga   15600
ctcaaaactt ttctgggcaa tgttccatgg tattgatgca gacgctttat ctaacatagc   15660
tcttgatagc tggctagcag agagtaatca actcccacca tccaatggaa ggaatgggtg   15720
gacaagctga atatgtcaag aaaagtgaga gtctgaatac actgatattt tgtaattaaa   15780
tatggatttg attgaggttt agaaaggaga acggatgaag ctgctggtgt gtggaagatt   15840
gcaccagaga gagaaaagta gttttaggag tggatgagta aaatactgca tgtgataaag   15900
```

```
ggtttaaagg aaaacaagag agaccagtgg ccattcaagt taactgagct tattttcaca    15960
agtatttgtt gagcattgac tatgtgccag acactgtgtt aagaggatgc aaagacatgg    16020
atatggctct gaagaaagag cctagtgtag catgcagaca cataagttta atatgtgaca    16080
ggaagaatga ttacatgtgt gtatacacac atgcacatag aatctatgta atattgagga    16140
tgaaatgatt aagtctgtct gggaaatcag ggaaggtttc agagaagaca ggacatctga    16200
ccaaggtatt aaagtgtgaa tgggagtttg ctaaggggat ttaagcatag gcagtagcat    16260
ttacaaaggt gcagtggcat caaccagccc agtgtgttgc tcaggagtac tgtagcacaa    16320
ggaagggta taacttaagg ggaagaagaa gaggaagagt atgaggcaat gggcctccag     16380
tggagggttt ctttgcagtg cccagaaact tgggatttaa cttgtgcacc tgtgaacctc    16440
agtatgtttc aaccccagag cactggaagg ataggccaca ttttttgcaag tagcagagta   16500
ttggcttagg aaagcatgtg tagatttaaa ttcctcctac aaactgcctt ccaaaaagat    16560
tacaatacat tcctccttca aggaaagaac acttgctgat agggaggcat tgaaggattt    16620
taagaattgt ctggtgtgat tgtgctttta aatccctcca ggagctgtgt aaaggatgca    16680
tttgaagggg tcaagatcca acgtgggtag aacagttagg agagagagca acagtctggt    16740
caagagacag tgagggcata aatgagacag ttgagctaga gggtcagcga tatattgtgg    16800
agatcattct aagctaaaaa ctaatgttag caatagaggt ttggggctgg gcgtggtggt    16860
tcacgcctgt aaacccagca cttgggagg ctgaggtggg cggatcacga ggtcaggaga    16920
tcaagaccat tctggccaac gtggtgaaac cccgtctcta ctaaaaatac aaaaattagc    16980
tgggcatggt ggcacatgcc tacacctgta atcccagcta ctcaggaggc tgaggcagga   17040
gaatcacttg aaccagggag tcggaggttg cagtgagcca agattgcacc actgcactcc   17100
agcctggcaa cacggtgaga ctctgtctca aaaaaaaaa aaaagaaaaa gaaaaaagaa    17160
agaaaataga ggctccgttg aatgtagggt ggttggtgag aaagaggtag gagaatagga   17220
tgattcccag gtttctggct tgtggtgcag gagatgagga gttcttgagt tgcaggctgt   17280
gtggttggaa agtgagaagg gagagttgaa agatgatcat ttagtttcat tttggaaact   17340
agtttcattt tgacattctt atgggaagga catcaggtag atgctcaa ggagaagtta    17400
taggcacaaa tctgaaatgt gaaataaagt tcatgtttag gaaaaacaga tttgtgaagt   17460
catctttaat ttactctgga tagaagtaga atgagagggc aaggctgcaa acattaggag   17520
gtaacagtcc aaggcagctt gagagaaagg ctatgtctac tttcatctct ttaccctcca   17580
aaaccctac acagtgtttc aaacagagca gaccctcaat aattgcatat cttacttgtt    17640
aggttgagaa agaaagaagg ccagataact atgggaagta acttgattcc gttggaattc   17700
ttttgcataa taaaatctga tatgtaatgg atgacaaatg agataatatt tacctgttt   17760
tcagcatggg tcaacaaaat acaagtactg atggctgctg caagctttgg ccaaactaaa   17820
atccccggg gaaatgggcc ttattccgtt ggttgtacag acttaatgtt tgatcacact    17880
aataaggtaa tgctttgatt tatacaactt atcctgatac tctaatattg tctgtcgcta   17940
tggaccacta gaaggtgttc aaatgtgacc ttgccctcac ctgagaatga ctcattttgc   18000
aatttgtatt gtttcatatg aaggctttta ctagtttggc cattcctcaa ttctttgtta   18060
ttgtctgatt aatttctcta taaaccttat ttttcacttc cttaataccT gaagccaggc   18120
tgcttgtatt ttcctttcac tgagatagaa tattgttttt ctgtttctct ttcatgacta   18180
tcttcaatca ccacagcagc ctaaaaagtt ctttagacct ttttgtgaac acagaggtat   18240
ttgagtcccc actaattaaa tatgcaaaat agctgctgga atatgtttga gacacaactt   18300
```

```
ctctaaaagt gcattaattt ctttcttaac agggcacctt cttgcgttta tattatccat    18360
cccaagataa tgatcgcctt gacacccttt ggatcccaaa taaagaatat ttttggggtc    18420
ttagcaaatt tcttggaaca cactggctta tgggcaacat tttgaggtta ctctttggta    18480
agatttctgt tgatccttct ttgtaggctc ttgcatgtat gaaaaccttg aaaacaacaa    18540
gaacttcaag tagttaagac caaagtagat ttttcttcag tccaaatagc tcctaaaatg    18600
ataaggaaag tatttcttta aagcccaggc aactacgaca gaatcaaggt tctcattttg    18660
tccattctga gttggatggg agtggccgag agtatcagac tgactctgac atctttctgt    18720
ggctgctctt tagttttcat ctgacatacc atggagaagg caataccgtg gtgagaatag    18780
caggttattt ggtgtggcca ctatcccgca tgctctgtgc taaagttaga caaaagaga    18840 aagaaagtag aagccatcaa actctccaga tccaaaacaa aggagtcaaa gctaatgcct    18900
ttcttgtcat acatgaagag actctactct cattcccatc acctaccccc atcgctaaga    18960
caatctgatg tgtattcttc acttactgtc tacattctgc taatatagac ttttccttcc    19020
ttatctgttt gactagacac tactgttgga ctgatgttaa ctgtgtcttc acatttaccc    19080
ctcaaaacga tctacaaatt tgggattca tcttaaacat cggcttttaa ttttcttaaa    19140
aaccacttat aacagacatg aaaatagcat aactctgcat atttatgttg caaaataatt    19200
tataaatcac ttccatagca atcatcacat tcagtcttta tgactgcatc tgcattttat    19260
agatgagaaa atgaaacaca aatgattgct gataataatg gtgacaataa aaattgagaa    19320
gtgaaagaag acaatatttc catttttga gccccttact atgtgatgga ttgcaccact    19380
gctttacata tattacctaa ttaaataaaa ttctcacaaa aaccctatga aagagatatc    19440
attttctgaa gttacagaa gaggaatctg aagtacagaa agtttaagga acttgcccaa    19500
gatccatagt taggaagtgg cagagctgca tccatgactc agtatgaagt cagtggtttc    19560
tctacccttt cctgcatgat tatgaccaaa tcataatgaa cagagtctct gtttcttaga    19620
ttctggctct tagtgtaatg tatccaaggt tttatgggta gtttggtttc agaacattcc    19680
ctttaaaatt ttttccaaaac ctgggaatgg cagtaagtag cagcctttat gaatacacct    19740
ataagtggga aaatctctca ccttaagtcc agagctgtca gtaagaactc atcgttaatg    19800
atcctatggt ctgaggaaag aacttacgcc gggtgcggtg gctcacgcct gtaatcccag    19860
cactttggga ggctgaggca ggtggatcac ctgaggtcgg gagttcacga ccagcctgac    19920
caacatggag aaaccccatc tctactaaaa atataaaatt agccaggcgt ggtggcgcat    19980
gcttgtaatc tcagctaatc gggaggctga ggcaggagaa tcgcttgaac ccgggaggca    20040
gagtttgcag tgagccgaga ttgtgccatt gcactccagc ctgggcaaca agagcaaaac    20100
tccatctcaa aaaaaaaaa aaaacttaca gttcagctct ttggttggtg ggtatctagt    20160
agcagtcttt ttaatgaatc tactattcat ccataaaaaa gtagatataa atcagatggg    20220
tctgcatttt atgctaatga gatatgaatt aaattcacta gcaacactca gagaaaacct    20280
taactataac cttccattgt tgtctaggtt caatgacaac tcctgcaaac tggaattccc    20340
ctctgaggcc tggtgaaaaa tatccacttg ttgttttttc tcatggtctt ggggcattca    20400
ggtaatgttt gagaggttga acaattttgg cttccaggaa taaatgacaa ttttttttatt    20460 caagaaagaa atagcagagt ttggaatgtc atgcaggccc ttgtctggag gagttgggtt    20520
tcctcaataa ttggctgtgg gtctattgat cagtcctaga cctgtctggt caagtagttt    20580
tttccctact atcagctcat tgggattagc ctcacagcag agaagaaagg gtgttgcatt    20640
ttctatagtt gtccttcatt attgtaatat ttacactctt aaaattatcc tctgtaaagt    20700
```

```
ttagaacttt tgagaaacca attttagatt agctgggaaa gactgttatt aagagaaata    20760
tctgtgaagg caagagaagg agcaggaaaa gatggggaga acctttggac catgacacag    20820
gttggacacc tgaaaaggtg atggggaagg gagaaggatt ggataagaag agcttcagaa    20880
tgaagcatgg ttctaagaaa tattgagcca ggccaatgga aggagtgctg gactatattt    20940
gcttatcaag agtcctgtat ctcataggaa tgggctaatg ttagtaccca tgctgtgcca    21000
agtctctggg agcagctcac tggatgctta gcttccactt gaccatggtg atggatacag    21060
aggggcagga gctggatagg gtctttagta agctatgcag tctgtagcat gatagctgag    21120
tggcacattt tcataacaac aaccaccctc ttcactttct tccaccactt tctcacctgt    21180 caccccctctt ctacttcaag ggattgtaaa actcagaaaa taagagagat ggcttttagc    21240
tgggaagaag ttgggtagca cttgcaataa agaattctct tcagcactgt aaatgtagtt    21300
cagctagcta tttgatttct cctacattag tgactggcaa attagaaccc aagggccaaa    21360
tccagcccac tgcctatttc tataaagttt tattagaaca cagccacacc cattcatttt    21420
tgtacactgt ctatggctac ttttgtccta caacagcaga gttcagtagt ggtgacaaag    21480
actatggccc acaaacctgg aaatatttac tctctggcct tcaacagaaa aagtttgcta    21540
atccctgtgc tatatcattc ccccctcttg aaaaggtcct gtatcttcag caataaataa    21600
atagtttcta gctacctcct ttttattctc tgtggacatt tcctattgaa tgcatggtat    21660
gaggaaaagg ttgtgcaaat gaagctgtgg aagagggcat aaatgcagtg cttagcacat    21720 gattttcaa ctatttcacc cagtccaatc atttaaataa tagctaacat gtgttaagta    21780
tttacctgtt tctaatataa gtactgaaaa tgtattaatt caattgatcc tcactgatga    21840
ggtagcatac tattatagtg tcaccatttt atagataagg aaccaaggca gcaaaaatat    21900
tgtgacttat taaaggtaca cagctaacaa gtggtagaac cagggttcaa actcagtggt    21960
cagactgcag gtctcattct tgtaactaca atactgtact gctttcctat atacattatc    22020
ttagcaaaac cttacaacta ccctaaaaca aatgctttac tcttaggccc attttacagg    22080
tgaggacaaa aatgcagtaa ttacctaaaa tcatatagct gggaagtggc agagccaaga    22140 ttaaaaccc aaaactctca aaggcaatat ttataatcac tgccctgggt tttctcaact    22200
ttagtagtct tgacattttg gaccagataa tctcttgttg tgaagggttg ccctgtgcat    22260
tgtaggatgc ttgacagcat ccctttaccc actagacacc agaaatacc ctcgcccacat    22320 tcatgataat gaaaatacct ccagacattg tcaaatatcc cctaaggaac aaaatcaccc    22380
tcctttaaga accgtagctc tccactccac cccagggcac tactcagggg gtgtaatggc    22440
ctccatgttc ccagttttat tagtggactc agccttgtaa tcatgactgg tagttgtaat    22500
tcttccctct ttttgttttg aaggacactt tattctgcta ttggcattga cctggcatct    22560
catgggttta tagttgctgc tgtagaacac aggtatgtta cctgatataa ttgggctctt    22620
tggccaacta cagggaatgt caatgctcat aactatgttt ctaattttca taaaagttta    22680
tttaaaatgt tgatggaact ttcaagtatg gtaacatcat gagcaaaaaa ggagattgag    22740
tttatcgact taaaagactt aaaagcaccct aacatttcta gagtgtttat tgcctgccat    22800
gtcctatgcg aaatgttttt aatacgccat ttcattcagt cttcataaca atcctatgag    22860
atggttatta ttattattgt tgttgtttta aggaagagga atatagaggt gataaagggt    22920
aatttgccca aagtcacaca actagtaagt ggcagtgccg ggatttgatt cctgagactg    22980
agtttcaaca tggctaacat tgcctcccag aattaggaag atagaatgga ttgagtttac    23040
ctgcaacttg atgatagaca ataaggtttt tttcctggaa ctcttttaca gtcttcttta    23100
```

```
atttaagaga aaatatagag tggaagaaga aagggaagtc aaaagatcag aggaagttga    23160
gtcaaggatg gaactgagaa acatgggtca gatgaggaag ggaaggagca tgcataaata    23220
ataattttgc ttgtattata gagatagatc tgcatctgca acttactatt tcaaggacca    23280
atctgctgca gaaataggggg acaagtcttg gctctacctt agaaccctga aacaaggaga    23340
ggagacacat atacgaaatg agcaggtaca ttgcagtgaa aggagaggtg gttggtgacc    23400
taaaagcatg tacaaaagga tgacatttgt taatttaatt ttacacctgg caagttatgc    23460
tcctagctct cctatttccc attcccaaaa gatctgtcaa tagattcctg gagcagtaaa    23520
attcccttaa tggaatatct agttcatagt aaaaacaaag gcaaatacaa aaatttggga    23580
gatgacagtg aatattcaga attcccttga attaaaactt ctaattttag aatctaaaaa    23640
gtgctagaaa ataaattaat agattcttcc tcacagacaa tataaaaaga ctactttttca    23700 gagaggcagt atacaataga attaagagta tgggccttag aacccaactt tctatgtttg    23760
aatcctggct ccaccactta attttgttat agaataatga atagaaacat tatttgtctt    23820
acagagctat tagggcagtt aagttaagtg aagcatattg gcttcctctt tatagtgggt    23880
gttttacatg tgttattatg tttgagtcca cccacatttc ctttaggtag gaattattat    23940
acaatcaatg gaaactcaga gaggttaagt aaatcgtctg aagtcacata gtaggtaagc    24000
aacagagcca ggatttggac taagctatac ctatgtgcaa agctggggcc tgtgtcatta    24060
tggtagcaag taatagtcac taatcagatt tccagtttat aactgaccaa cgattttttcc    24120 caaatacagc ttctacctaa actttaaaat aagtgttata acttttttact ttgtcatttc    24180 cttcttctaa taattatatt aggtacggca aagagcaaaa gaatgttccc aagctctcag    24240
tctgattctt gacattgatc atggaaagcc agtgaagaat gcattagatt taaagtttga    24300 tatgaacaa ctgaaggtaa gctataaaaa gtaatttttc tcttgtccta cagttcttta    24360
ttgttttttg tcatttaatt ttctgctata ttgcaaggta caatatgata aagggctgca    24420
accagccccc tccccaatgc gcacacacag acacacaaag cagtacaggt aaagtattgc    24480
agcaatgaag aatgcattat cttggactag atatgaaatt gccaaaagtt agtcagtttt    24540
gatctacaaa aacagcaatg tcatatggtt caactcaact cctgtggaag tattattatt    24600
tcatggacag ctcctgcatg tttttaagct tgatcttgaa aacttgacac aagtttggga    24660
gcgggtggaa aaatatcaga cagagtgggc agcatgaaca aagactcaaa agtgtgtgtg    24720
gcatgtgaag tgcagggatt aggggggaact agagaataag atgatggtct gttctccaga    24780
tacaatgaag aaatttgtta tccctcaagc agccactctc ttctgtatcc ttgcctttgt    24840
acatgttgtc cccttggcct gacacaccct tcccccttgcc taactcctac ctaatttcaa    24900
gactccagtt gagcatcacc tcctctaaga agctttcttg gacccccaata cccacttctg    24960 gactgggctc gctgtctgtc atgtgtgctc ctttgtacca ctgtactgta ttgcatcatg    25020
cctctgtata actttcttcc ctgatggact gcaaactcac tgaaatgaga ctgcagtacc    25080
tggcacagag taggtactca ataaatactc atggaatgaa caaacaaata aacatggggt    25140
gaggagaggg agaagtcaga actgatgttg aagtttccag tgtgggtgac tacaaagaac    25200
attaagttta ctttcaaacc tttacatatg ttatatatat gtgtaaatgt gttttatatg    25260
tgtatataga tgtatatgtg tgtatggtat gtataaatgt atgtgtgtat atgtatattc    25320
tattttataa gaaatcaatg tatttaacca tccccatgaa atgaacaatt atatgattga    25380
caaaatcatt tcttctaaca ccacgaaata gctataaatt tatatcatgc tttttcaaat    25440
aggactctat tgatagggaa aaaatagcag taattggaca ttcttttggt ggagcaacgg    25500
```

```
ttattcagac tcttagtgaa gatcagagat tcaggtaaga aaataagata gtaaagcaag   25560
agaatagtaa attattggaa gaaattatat tgtgagatat aatttttat tcaaattctt    25620 agtgaagaag ggatctcttg gagtttataa ggctattctt ttgcccccat aaaatactct   25680
atatacattt tcctaggcta aaacatctac ctctcctgct attaaaatct ccccctactc   25740
ccataagttt tccctcatta ttcttgttta cccaaggggt taacactttt cactgaaaaa   25800
tttatcttta tataattttt tgtgacataa tgattgtgat aataatattg tcatcttaac   25860
agtattgcca gacttctcca gtgggcagga catttttaa ttaggttttt cccccttcca    25920
cctttaagat ggagctggat ctaaaattac aattatttgg gtaagagttg ggacaagacc   25980
ccagttttct agcttgcagg aacattttct ttcttaaacc ttcattccag actgatgaga   26040
tcacatagaa ccaaccgtac agagagtggg caggatcatt tttgaaactt cacctcaaat   26100
ttcttaaaag tccatttcag tgtaagaatt ctcttctttg atccatttac caaaagatca   26160
ggaaacatag gataaactta cttttaaaaa ggaagttagt ttcatcttca aatgatatgc   26220
tccatatgtt tttcttcaac cctcagacag ttttttcagct gaagtgcctc taaatataaa  26280
gtaatgggcc caattgttac tctaataaag ctataataaa tacactacaa ggtgcataaa   26340
agctctgaaa acaaaggtgt atttattata cttttttcaga tactccacag tgttgaagaa  26400
attattatgt attctaaaat ttattttgaa taaaaagttt taaggatata tcactcaaat   26460
ggttgcaatt cctaaaggca tataaagaaa atgattatat aaaattccag gtctgctact   26520
ttacaaagtt aatcatatcc ctttcccaca ttgaagtatg ataccctctt attccaatga   26580
gataacccat aataaactgg tatggtgcgt gtccaccaat cctagcatta ttaggatgtc   26640
ctcaatgttg gctagtatgt aaccagttta atttcatcat tgtcaacaaa tatctacaga   26700
tgtggtattg ccctggatgc atggatgttt ccactgggtg atgaagtata ttccagaatt   26760
cctcagcccc tctttttat caactctgaa tatttccaat atcctgctaa tatcataaaa    26820
atgaaaaaat gctactcacc tgataaagaa agaaagatga ttacaatcag gtaagtatta   26880
gtgacttatt tcattatgtg aaacaaactt gaagcttggg taaatatcaa tcgatatcat   26940
ttggtaacta ttaaagaatt gctgaattgg ttgtttagac tttcaataag gagagaatta   27000
gataatctca gtttctaagt acatttagtc ttactctttt taaaatggga atgttaacgt   27060
atatagtata tatactggtt atattagtct gttcttgcat tgctatatgg aaatacctga   27120
gactgggtaa tttataaaga aaagaggttt cattggctca cagttctgca gcctgtacag   27180
gaagcatgat gctggcatct gctcggcttc tggggaggcc tcaggaaact tacaattatg   27240
gtggaaggca accggggcat gagcacttca catggccaga gccggaggaa gagagggatg   27300
ggtgaaggta ctacacactt ttaaataacc aggtctcaca agaattcact gtcacaatga   27360
cagcaccaag ggggatggtg tgaaaccatg agaaactgct cccatgatcc aatcacctcc   27420
caccagtccc tgcctctgac actggggatt ccaatttgac atgtgatttg gtggggacac   27480
agatccaaac tatatcactg gtaattaaaa ttagcattat actacatgct acttcaatct   27540
aaacaccaga atatgcctac agattttggg gggtagagct aggggaagt attccatcat    27600 taggctgggg taggaactct ttaaagaaaa agtcagatta tcgactgaga cctgcaatat   27660
actaacctgt tgagaaagaa tatgagttta taaattcccc aaagctataa tggggtacca   27720
tgacgtgttg gcaattcttg tatcctggag gtgaaaaaga actcctgata aggttttgaa   27780
ctctcgatga gatattacaa agcaaagatg gacctgaact cacccctttc ctatctgaaa   27840
tctggtttat ttaggagaag agaagaggca ggaaggaaat atatgagta taggcaataa    27900
```

```
acactatggg ctcagagaat agaggggtct cttccaacag aaaaggattc atagatgaca    27960
ctaaaattgg attttgtaag atcaagagag tttagatagt aaggaagggt ttaggtattt    28020
caggcaagga cttcatttag cttatgtgta tgtgcaactc tttctaattc taaaacggaa    28080
ataatacaga acacctaacc ttccctcaac cctatttcct tactaagctc tcacctttgc    28140
ttttgtccct tctctgctag aaaccttcaa agaatagcca atattagtca ttgcatgtgc    28200
ttacttctat tcactctttg actcttgtgg tctagcttcc tgggccccca cgggcatgcc    28260
aaaacaaaga cactaaaggc ctgctgcctg ccacaccagc agcctcttca gagtctcaac    28320
cttgctctct gcatctgttc aacattgctg accaccccct ttcctgctcc cttggctact    28380
atgacccacc tctttgctgc ttctcctgtc atttataccca ctccttccat ttcttctcct    28440
ctggcagttc tctacagtca gatcatccaa gcttctgctc gcaattctct tgtattcctg    28500
ctgtttatct tctttatgtt tctgacattc aagtttccta ctacaatgtg gggaagagtg    28560
agagggagtt aagtggccct gttttgagct tagatgacta aaagaatgat gggttgctta    28620
taagaaccag cagagtcaag aggcagagca gctttgggca ggactgggaa gatgtctttt    28680
aacttcacaa tttcttagct tgagaactga ggaatctgta cacagatgtc tggccacaca    28740
ttggatgatt acataattta catgataaca cagatgaaac atttgaagta aagagattg    28800 caaagtgaga aaagagttgg tctgccagta gaatcctaag gaatgcctac attcagccaa    28860
tgggaaatgg gtgaagagcc agtgaagaac atagagtggt tagcgtcaga agggaaggtg    28920
caatgttaag gaaacgtaaa gaaaaaaagt gcaagaaggc catcaagtgt caaatgtccc    28980
agtggtggta gaaaacgagg acttaaaaaa ggccattcta tttgacgtta ggctattgat    29040
gaatttacag agcagtgcaa atgatatttta taaagtgctt acagtttaat actgggaaaa    29100
gtggtgtttg aaatctgttt cctctaaggc ttaaatctaa agtgatttaa atttaaagtg    29160
actagcatca aatacatacc acgttcagtg gtgagggcag gtagcaggct ctggctctga    29220
gttcagggac ccttcaatac agaacacatt ccagtattca aactggaagt attccaattc    29280
actaaaaagc aagaatcatt tcttctaaaa tcaagatacc aagcaagaac aagattctt    29340 gagttgtatt tctagaggga agaagaatat actctgggat ccctaaacaa acagcctgtg    29400
acccttgaaa cacatctaag tagatcaaat tacaagtttt atttcttctt tggttttcag    29460
taaacagacc aacaagacca gtacctttct tacactctaa ctaaaaaaat aataatttta    29520
tcaaacaatg tgacttttaa atgtcttgtt ctcttttagg ggttcagtcc accagaattt    29580
tgctgacttc acttttgcaa ctggcaaaat aattggacac atgctcaaat taagggaga    29640 catagattca aatgtagcta ttgatcttag caacaaagct tcattagcat tcttacaaaa    29700
gcatttaggt aagaaactat ttttttcatg acctaaaccca gatgaatctc aggacaaagc    29760
tgtctatctt aatacagctt tagtactatt taaactattt ccagttggtt tacaatggaa    29820
caaagcagta tatcaatttg aaaacagaaa tttgagaaag tcaattttgc tgctttacat    29880
cctctatatc atagaaagca aatccaactg ttaaaggtaa tattctttgt atgaagccta    29940
gagtggactt ccatgttgag gatactgaca gcaggttgcc tcactcctat cccgtttgca    30000
ttcagctgct aaagcagcca tgaggcagct gatacagagc acatcgtctc taccatccta    30060
acggaacttg tgtaatttgt aaatctttat tgccacctag gggcaccaaa ctgtttaatg    30120
ctctcaaaag tttaatatgt tgattaacac tttatatttt ataggacttc ataaagattt    30180
tgatcagtgg gactgcttga ttgaaggaga tgatgagaat cttattccag ggaccaacat    30240
taacacaacc aatcaacaca tcatgttaca gaactcttca ggaatagaga aatacaatta    30300
```

```
ggattaaaat aggttttta  aaagtcttgt  ttcaaaactg  tctaaaatta  tgtgtgtgtg  30360
tgtgtgtgtg tgtgtgtgtg tgagagagag  agagagagag  agagagagag  agagagagaa  30420
ttttaatgta ttttcccaaa ggactcatat  tttaaaatgt  aggctatact  gtaatcgtga  30480
ttgaagcttg gactaagaat ttttttccctt tagatgtaaa  gaaagaatac  agtatacaat  30540
attcatatca gcctaaattt taattttaaa  gatgattcct  tttcagtgtc  gaagttaaaa  30600
actgttttta cattactttg acagacaagt  agattaaaac  aggcaaaatc  ccagtgaaaa  30660
cctgttgcaa tgatacaaga ctccctaaac  atagagtaaa  aaacaatttc  ttgccttttta 30720
ttatctacta tgggcagtgg agtttaatta  tagcaacatg  atattctagg  tagaatttgg  30780
cagctcttct ctttgacttt tggtcacggt  aagaaaaatt  agaacaagca  aaagccattg  30840
tttcagcaca ggattggtgg tactacacaa  tttcaaatga  tgactaaaag  gagtagagaa  30900
gggttaagaa tattagagat gaggcaaagg  cagtggatta  aattggtaat  tttttgacac  30960
tttcttttaat tctttaaggc attctacttg  ctaaagaaag  gttcctcagg  tattacagca  31020
tatagcaggg attccagtta gaatacatta  gttactcaca  caaggctgt  gaaggataat  31080
aaaacattca gaattacatt tagcttcttc  atattccagt  taattttatt  taatgttttc  31140
aattctatat gtagtagtaa aacagaataa  cacgattaaa  tggaggtaaa  aatatagctt  31200
aagaatgtat acttataaat atgggaatca  tggaaaatga  ttttatttcc  caggggacat  31260
aaaaatttat accactcatt tggtaccccta  gtcctatctt  agtggtgtca  ggtgcaaagt  31320
cactcattct gagaaatttt acttctgtag  ccattcagat  taaattttt   aaaatatggga 31380
gttaaactca gcttgaaatt gaaggcttcc  tataatctga  tcctaatgca  tcttctctga  31440
gctttgcttc tggcaattca cattatatta  tctatatgag  taagccaaac  ttgtctattc  31500
attattccag gaataagtaa tatactcatc  tacctcaatt  acttttaatg  caaacctctc  31560
tcccttctac ttacggaaat tataatgggt  ttttaaggtt  cataattcta  tttccattag  31620
gcttcagagt ctgataatgc ttcacagaga  tacacctttta ccccagtctc  atttagcaaa  31680
cctttttccct attcattttta gaaataagca  ttccaactgt  atggatgtcc  cattcaacac  31740
tttttttgttt gtttgttttt tacagtctttt tgttggtggc  gcatgctgat  gctgaaagga  31800
gaaataact attgaaaata tctaataagt  taaggttaaa  aagaaataac  ctaacatagt  31860
gcacactgag tattttttcag ggtaaagaaa  gacacattta  tcaaatgcct  actcctttttc 31920
agggacttta tatcaattat ttctcatctt  aaaaaaacac  tgcaagaaag  gttttattat  31980
caccacttta cagatgaaga tcaaagttca  aaatattaca  taatttgccc  atgtcacata  32040
tctgttaagc agcatatagc tcagatctgt  ttctaaaagc  taagatctat  gctttgcaaa  32100
atcatgttta aaaagtcatg ggcttcaaag  ttaggtaggt  ctgggtttga  tcaagcctct  32160
gagactcatc agctatctga ccttaggcaa  gttatttaac  ctctttatga  agcttcaatt  32220
ttctcaccta taaaatatgg ataatattga  tatgcacttc  aaagttgatg  aataaagtga  32280
aaaaatgcat ttaaagtata agctaagtga  ctaatacata  agagctaaca  tttaatatta  32340
ctatgctttc cccaatcctc cattacagag  gagagatgga  accaagtata  tttaagagtt  32400
ctatttcctt tttaataaaa tgagaccatc  atattaagga  taaactttat  ttaaggataa  32460
acttattca  aatcttgtat tagcatactt  caaattcaaa  cagaatgtta  gtcaaatgtt  32520
tagacaaaca ggcaaagatt cagagtcaag  acaaaaattc  tgaaggagga  tctgctaata  32580
agctatctaa gtagaatcaa ataatgtact  tgtcatgagc  ccttattttt  ctattttaat  32640
ttaaacactg tatttgaaag gtaccaaaat  agttttttgaa atgtaatgtg  ttagtaaact  32700
```

```
gtttagcaaa ataaatcctc ccaactaatt agaaacgtaa gacaataaag acgaaagatc   32760
ccagatctgt atatataaca ggatcactat aaacacaccc caccatcaac ctgagaccta   32820
atttgttttc cacctatata gaagttttg aaaatgacaa cttcttgtgg ttacatgttt    32880
tcaattttct caaatactct gttggtctgc gtaagatgcc acttgttcaa gggcagcttc   32940
tgactgattg ccacagcta tagatccacg gttaaatctc catcacctcc aaaccccttt    33000
tctgaaacaa aaagagaaaa acttcaaact gagaaagaaa catacaaaca aaaaaattta   33060
tttccatggg tgttaccatg acaaatgtaa tgttctctaa aagggagagg ggacagatga   33120
gtattctaat tactatagg cattatttct atagaaacaa tgttttattt tcttattaat    33180
attttggttc tcacactgta ccatcaaatc aagtttctct aaaaattatg aaattggcat   33240
attttatatt ttgctagaga atggtgtgaa caaggctgat aatcaattag ttcttttcc    33300 tttttgatta gtatatattt ttcacatgat attaaagcta ccattagctg attttattct   33360
caatgtgcct caattctaag aaccactgca ttatttatga acaagaatgt gcaataccaa   33420
gaaccagcca ataatttgaa tcttatataa actaaagatt cagaaattcc aagagattat   33480
ttaacaaata tcatttgaac atatgagcta attaacagag aaaattcttt aaaatgtgaa   33540
tttatcacat tcataattta actttcaaga ttaattcaat taataaattt cctatatttc   33600
aagaaatcct catcttgggt tatttatctc cataagtata tttaaatttt tttacctaaa   33660
gtggtttttc ttccctgcta cctatgtcca aagaaattga taaaccattt ttgtttgagg   33720
gattcagcat aacaatattt ttaagaaatt gtaattctgg gtgataaaag tattttgttt   33780
taaaaacaca agttacccttt aatagtggta tcacccactg acatgaagta aagatctttc   33840
cctactcttt gggatacagc ctaacaaaag gaaccctttga attgctattg attcttattc   33900
acgagtacaa aataattcaa atcagaaatg gaaccacaga taagccagaa aagatgtaaa   33960
caacaaaatg tatttctatc aaaattatga caatctgatt ttataatgag gaatcatgtc   34020 aagtacttt tctattcttc aaatactcat ttctctagaa catatccctg gagcactcta   34080
cacagggagt aaagtaccct tttccaatgt ttagctctca aatccccaac aactctggta   34140
attggtgaag gaggaggga catcattgtt caagggctg ttattcaaac acagtatcca    34200
tgtagagcca cagatgcttt attaaggaca atgaaaaggg aaatatttct cctatattcc   34260
ttttaacaac caatagcatc atgtgcatgc attatgtgat acagtaacta acaaaatact   34320
cttatggtaa aataaaataa ctcagataag aaaccatttt tttaaaaaaa gtaattagat   34380
tcctagatca tagtgacttg atgtatcatt aaaaaaaagt catgcataat acaacactca   34440
ctttgtaagg aaagctagct catttgtaga caggtatcca gagttaagag cttcctcgaa   34500
tttgagggaa ggatatttaa atctcattag taaccaaatc aaaattttta gagtcttact   34560
cataagtagt ttctatatgt ctgctaactg gcctagtcaa agccagaggt agttatctat   34620
ttacttatct agatatataa ttttatgtct actttaaata gttcttttct atgtagcagg   34680
catagagaac tttatccaaa ctgaatcttg tatgtacata tgtatgcatt tggctgtgga   34740
ttcttcataa ttaatggatg gagacaaccc aaatgtaaaa agttttagta aatactgatg   34800
caaaaagtgt agtaggctgg tattttgac ctaagcaaaa aagtaattaa cataaagaga    34860
gatattcatt gatttttat agtaaaaatt tcaaatgacc taaatatcca acactatggg    34920
aaatggttta atacattatg gctcactagt gtcatgcagc attatttagc tattaaatat   34980 tgttatggc cttctgggtg cagccaagat ggaataagct gactataacc tctttcgctg    35040
attacaatga aaaattctag acagaatata aaaagcaact actcaaagac tcaaaagtga   35100
```

```
acagaaatag gtagattaag aattaaagta aaaacgtgaa taatgactca caacaggagt   35160
gagtttcata ggccttttct tttctttttt tttacttctt tgtctcctga ttttgatctg   35220
agggtgggcc aaatcaaaac tgcctagcta gcgtagacag caaaactctg agagaaattt   35280
cttatttata gccagtggac tagggataaa ggaaccctga atgctagaga gtaagaaata   35340
ggtaggaaat ctctttgctg tattgtggtg ttatgtttat ttctattttt ttttctggcc   35400
ctgccctgag ggtggctaac cccagttact gcctggtgac agctatggca acataggcac   35460
ctacaaatgt gagagatgac ccgtctctct agccagtgga accaggaaaa gagctttctg   35520
tcatctgaag aatagtaata ggagattgtt tttgttatct ctttatctgc ttcgctctta   35580
cgggcaaaca gaactgtgtg gtggagcaga ggctgagaga aaaatactgt ctggctaggt   35640
gaccagaaaa agggggccatt ggaggctgga taagagagga tcctgggagc agaaaatgt   35700 ggaggacatc tcagagagga aaggagttga aaatgtttaa ctcctaatgc tacatgtgaa   35760
ctctaagtct caggattgcc cctgagctat gcacatgcag aacagagcca ataagcaca   35820 gcaaagtctt tgacacttaa ctactatata aaccactgac caaagtccct gactaccctg   35880
ggtggcttat gtacctggaa gacctgaaca acaaaggctt tgaaaactaa actgacagga   35940
caatcaccaa ccacagaagg agaaagagaa catgtaggat gaattgaaac cagctgatca   36000
tctgctgtaa caaaaacttc aacattctcc agattttaac aggacccaat gtcttaaaac   36060
ataatatgca aaatgttcag gatataatcc aaaattactc aacatacaaa gaaccaagaa   36120
aagctgacca tttctctagg gaaaagaaaa tcaacagcta caaaccccaa gatgaccaga   36180
tattaaaact atcagacaaa gattgtgaag tgagaagttc aagaagtcca accaacccca   36240
aacaggataa actcaaatgc ccagacacat cataatgtca tggcaaattg cccaccatat   36300
agtcttaaat gaagaaaaac agaatataaa actatacata ggatgaaatc aattgtgtct   36360
aaaatatgta gatgaaatac ttatattaca tataaacaga aaaattataa aagaaaacca   36420
aactggtcaa cctatttgtc tctggatggg tatattatcg gtgattgtta ctttctcatt   36480
tttaatattg ttatatttct caggtttcct gcatctaata tgtatttat tagagtcatg     36540 aagaccaaaa cattttctaa tcaaggagta aaacattaat aactagtttt ctcagaagaa   36600
tacttggcat aaggactaaa atcactgatt tgttattgc tgttttaac tattgtcaca     36660 ggattttcct cccattttc caaacacaag gactttggaa atagtttgtt aaatcacctt     36720
tcaaaatgaa gaacaatgct ctcactaatt actatttata gaattccata cctcaggtgg   36780
actcttatcc aatttgggta tgccattcca gacattctca gggttcacta tctcctccat   36840
accatttgaa aggttcaaaa cctacaggag aaaacaaatt ttttaaagt gtccaattca     36900 aaaaaataac tgatttatgt accagagcaa ttatttaaa aatgaaatac tattattatt     36960
attattattt tgagataggg tcttgctcta ttgcccagga tggagggcag tggcaggatc   37020
agagctcact gtgaccttga cctcctgggc tcaggcaatc tgcccatctc agcctcctga   37080
ataactggga ctacaggcgc acaccaccat gcccagctaa ttttttgtat tttggataaa   37140
gacagggttt cactatgctg cccagtctgg tctcaaactc cttggctcaa gcgatccacc   37200
tgccttggcc tcccaaagtg ctgggattac aggcataagc cactgcacct ggccctaaaa   37260
tgaaacactt taaagacaa tgaaatgaa tttattgagc ttcaacctta tgtttcaaac     37320
tccatgctac ttcagtttcc caaacatatg tagagtatct atgactggtg atcaaagatg   37380
gataaaattt caacatcaaa tagttcaaaa tctagtggag aaaagacctc taagcagata   37440
attacaatac accataggaa gttcagactt ctgtagtagg aggtatagga ttgtaataca   37500
```

```
gaaataaggc ttttttttggg atgggggaag gttgaggaca agaataaatt tagaaaataa    37560
catcagtgaa tgctccctgg tagaggcaat gggtaagtaa attggaatta accagtttgg    37620
taacaggatg gaatataggt aaaatagaac tgcaatatta aatatatcga aagagcaagc    37680
agatggtata tgtaagagaa gtcaagaatt ttgatgtcca tttaatataa agtacaaaat    37740
gtatagaatt agggccaaag agagtacata aacacttaac cctagaggat ttcctatgcc    37800
atgttaatga gcttgacttt tatgttccag gccaggggtc tccaatttta atggaatatg    37860
aatgcgtatt ctggaatcct aaccccagaa attctgaatt agcagtccag gcgcaggcgt    37920
aggaatctat aatacaattt aaaaaacagc cgggcgcagt ggctcatgcc tgtaatccca    37980
gcactttggg aggctgaggt gggcggatca caaggtcagg agatcgagac catcctcgct    38040
aacaagggga accccgtctc tacaaaaaaa tacaaaaaat tagctgggcg tcgtggtggg    38100
cgcctgtagt cccagctact tgggaggctg aggcaagaga atggtgtgaa ctgggaggca    38160
gagcttgcag tgagccaaga tggcgccact gcactccagc ctgggtgaca gagttttgacc    38220 ctgccccaaa aaaaaaaaa aaaaaagag ggaaatatat atatatatat atatacacac    38280
acacacacac acacacacac acacatatat acatatatat acacatatat acacacatat    38340 atattacatat atattacata tacatatata tatatatata tacacacata tacatatata    38400 tatatataccc aagtaactct cgaacaggtg gttttcaaat cacgggagaa acacgatcaa    38460
caggctccct aataagttt acacaataat gaagtaatca aatttacatt ttacaaactt    38520
caccctgaca ccatggacaa tcaatttaag gaagactaga agaagcaaac aaaatagaag    38580
gttattaatg tagttgtgaa atgactcaac taaggtagtg gcattagata taaaaaattc    38640
caactaagag ataagatgtg taaagtgtgg aactaggtga ctaatagcat ttagaaagag    38700
taagggagat agatgataca gcctaggatg attctcttgct acgattctta tatatggaga    38760
tttaaaatat atgtgcatta catcaagtta tcaggggggaa caagcaagta aacatttgtt    38820
caatcgcgtt ctctagtctg acagagtctg gtaaactttc cttaatagtc tgcaaataca    38880
tttggagata aagtacttaa acatcactta cccttgttcc ttcttcagct gtttctaaaa    38940
tctcacattt agaccatgtg tttcttagac ttgaccacac aacacatta gatccaacag    39000 taaaggcttt cagagtgtag gtgttctgta gttgagctgc caaattgaat tgagtaagac    39060
tcaatgcata tctcttaatt ccttaatgta acatacacaa gcaaagcatt ttcctaatct    39120
gcattatttc tatatcatca atatcatgta attagtacat tggtatgact gtctccctca    39180
attttgttta aaattcttac agtgcccgcc cccccatata atctcttatt gcttttctaa    39240
accaacaaac caaacaaaaa atcaccacaa ggatgtgaat ttgatttcta acagtgaaaa    39300
tcgctaataa aatatggtac tattaagaca agtggtgttt tttatactta caacagccat    39360
ttctataaga aagcagcatg ttacaaatga gcagacattc ttatcacaga gttaatacta    39420
ttattaaata tgcaatgag gaataaatat ctaatgcaag ggtaatactt aaataactta    39480
tgtgttaccc ataggatggc ataccatgca attaaaatat tttgaaagca tttttaaggg    39540
actaaaatgc aggattcaat actgtatgat agtatgatct aaattgtttt taaaactata    39600
tagtagacat acacaaagac agtaaaagac aacaaaaaga aaatacatca tggtgttaac    39660
attgatcact tcttgttgat tttcattctc actattccat tatttccctt attttttacaa    39720 tggttcaaat ttaataatat aaaaattgac atttaaaaag tatagcattg attataaaaa    39780
gctaaaagtt acccatttaa caattctttt taagtagcaa acagtagtaa aaataattta    39840
taaaaaagtt aataaatgtt ctccaagatt tacacatgaa acagtttttg attaatatag    39900
```

```
gctacctaaa tctatttttt ttctttaagg gtttctaatg aattgcaaga tcaatgcatg    39960
atacagttaa gtctaaaaga ccctgttgaa ataatcctta gtgtaaatta atgcctgtag    40020
tagtgccata aatttggcaa gggaatacca tgttttataa aacttaccaa cacatgccct    40080
cttgattata aatgtgatta catttttaaat gtgattacct tttggagact aatagatttc    40140
aagcattcaa cttttaaaca caaaactaat atttcagtgt tcttccagc acatattttg     40200 cactgatttc acaatatatt ttccccaagt ttaaaatgcc cttcataaaa tccaatctga    40260
ttcactttcc aggtttttaa tctcttacaa aaaattattt tttagaaatc catataagaa    40320
ttattctctt ttctttaaaa caaataacaa ctctggaaag tcactatgtt aaacttaaaa    40380
gtaaaagcac actttgggag gctgaggcag aaggactgct tgagcccagg agtttgagac    40440
caacctggat aacatgacaa accctgtctc tacaaaaaac agaaaaataa gctgggtgtg    40500
gtggcacaca cctgtagtcc cagctacttg ggaggctgag gtgggaaaat cactagagcc    40560
tgggaggcag aggctgcagt gagccaagat cacaccactg cactccagcc taggtgcacag   40620 agcaagaccc tgtctcaaaa aaaaaaaaaa aaaaagtaa aaggaaaaa aaattcacat      40680 acctgagata tgatctggta aaccattatt gtgcttgctt ccatcactgc tttcttcctc    40740
agagaacaaa ggcatcaatg ccgaaatggc atccctgttt ttatactcta caaattcttc    40800
ttcacatata ttcatttcat tctgtgtttt aggatcacaa tctgctccat gtagatgcaa    40860
tgacatcctg cgctggtcat caaaagattc tacacaactt gactttctca tgtcctcagt    40920
acacatggat tcctgtgctt tctgactaac tcctaaagac aaaggatcca tcttgtcatc    40980
taaaggcagc tgggctgtag gtagttctag ttctggctgt ttctcagctt cacagctgag    41040
aggaagctgc agtgtaaata gctccatggc gccttttgtg acacactctt gggagagtgg    41100
cacattcggt ggcaccgggc ttagctcccc ttttcttca tccaccacca gagaattctg     41160
taactcaata gattccagtt ctaagaattc ttttgattca tcatcaggag aaagcggcac   41220
ctcaagtgaa ttcagttcta gtatctcctt tgtttcatta gcatgtggta gtaatgtgtt    41280
aaatcctgta atcaggtatt tatcatcaaa ctctgctttg tcaaccagat ggcactctaa    41340 ttcacctttcc agttcctcag tatcaatttt atctttgcag gggttttcaa acccttcaca    41400
aatgttatca gttttagggt cacggaagtt acttggtttg gttccaataa tgtttacatc    41460
tttttcagtt atttcagcaa gctcatctgt ctgttgttcc atatatattt tattttgtac    41520
agctttatta cttaatttct taagtcctac atcaagattg taggacccaa gagtctgctt    41580
tatctctgag tcaatatttt catagggaag agcactttta ataccagtct tagaatattt    41640
ctccattttc tcattaatac ttttacccttt gcttttcaag tcaacaattg ctaaagggat    41700
atcacaaaca tcccttctga tttctagtat tgttatttcc aacacatctt ctgttattat    41760
ttcatagaaa tagtcatttc cctcttgaga acataatcct tctgaaatgt taaaccctga    41820
gaggcaacat ggaaaggctt gcatgggaac cgacagaagt tcagaaggaa tggcccagag    41880
tgcttttggg tccacacagt cttcaatgtt tccaaagtcc acaagcctga cagatacaag    41940
ataatcttca caaatattag tgataagtgc cctataataa tgtccatctt ctctgtatct    42000
tactatacaa ggatctccaa tataaggaca tgggatacaa tttctcctgt ctgctacctg    42060
ttctccagca gtctgtactt ctacttctaa acactgaagt ttctccgtat cagcaaactg    42120
acaccaaaag tactcaggtc catctatcac agtggcataa gctcttatca tttttttttc    42180
tggattatac cagttaagaa atactgaagt gtcaatgtct gatttgttaa cagactttga    42240
actggcactt ttaattactt gggtagaaag ttctacttga gatttttcac tgagagcata    42300
```

```
cctgctaatc atatcatctg ctatgatccc atgttcatca gcaagaataa cttcccatct  42360
gtcttgaaat ttaacaaatt cacatcttat tgcagcctcg ctggtccgtt gggaaaagta  42420
atgcatcatt ttcttagaat ttttattgtc aggaacctca aatccctgca aggagcaatg  42480
aatgcacaac cccggcaata ttgcattaac aaggtcaagc ctacctattt tgttagtatg  42540
aaccacagaa acattgccat aatctataaa ctgcacagag agaaggtcat tgggttgttg  42600
ctccttgatc a                                                       42611
```

ISOLATED GENOMIC POLYNUCLEOTIDE FRAGMENTS THAT ENCODE HUMAN LIPOPROTEIN-ASSOCIATED PHOSPHOLIPASE A2

PRIORITY CLAIM

This application is a continuation application of application Ser. No. 10/161,127, filed May 30, 2002 now U.S. Pat. No. 7,468,266, the contents of which are incorporated herein by reference. Application Ser. No. 10/161,127 is claims priority under 35 USC 119(e) to provisional application No. 60/294,404, filed May 30, 2001, the contents of which are incorporated herein by reference.

FIELD OF THE INVENTION

The invention is directed to isolated genomic polynucleotide fragments that encode human lipoprotein-associated phospholipase A2, vectors and hosts containing these fragments and fragments hybridizing to noncoding regions as well as antisense oligonucleotides to these fragments. The invention is further directed to methods of using these fragments to obtain human lipoprotein-associated phospholipase A2 and to diagnose, treat, prevent and/or ameliorate a pathological and/or medical disorders.

BACKGROUND OF THE INVENTION

Human lipoprotein-associated phospholipase A2, also known in the art as Platelet Activating Factor Acetyl Hydrolase (PAF acetyl hydrolase), is one of a family of enzymes that catalyze release of fatty acids from membrane phospholipids and can thereby initiate synthesis of proinflammatory mediators. During the conversion of LDL to its oxidised form, lipoprotein-associated phospholipase A2 is responsible for hydrolysing the sn-2 ester of oxidatively modified phosphatidylcholine to give lyso-phosphatidylcholine and an oxidatively modified fatty acid. Both of these products of human lipoprotein-associated phospholipase A2 action are potent chemoattractants for circulating monocytes. The enzyme appears to play a central role in the development of atherosclerosis and is regarded as an independent risk factor for coronary artery disease (Caslake et al., Atherosclerosis 150: 413-19, 2000). Specifically, this enzyme is thought to be responsible for the accumulation of cells loaded with cholesterol ester in the arteries, causing the characteristic 'fatty streak' associated with the early stages of atherosclerosis. Recently, medicinal chemists have begun to design and prepare lipoprotein-associated phospholipase A2 inhibitors for use in preventing or inhibiting progression of atherosclerotic diseases (See, for example, U.S. Pat. Nos. 5,981,252 and 5,968,818; Boyd et al., Bioorg. Med. Chem. 10: 2557-61, 2000).

The level of PAF acetylhydrolase has been found to be altered in several disease states. For example, acquired deficiency of PAF acetylhydrolase activity has been reported in patients with systemic lupus erythematosus, stroke and asthma, and increased levels of PAF have been reported in children with acute asthmatic attacks (see, for example, Hiramoto et al., Stroke 28: 2417-2420, 1997; Kruse et al., Am. J. Hum. Genet. 66: 1522-1530, 2000; Stafforini et al., J. Clin. Invest. 97: 2784-2791, 1996). Miwa et al. (1988, J. Clin. Invest. 82:1983-1991) have also described an autosomal recessive form of PAF acetylhydrolase deficiency which has been observed only in the Japanese population. PAF acetylhydrolase activity was absent in 4% of the Japanese population. This inherited deficiency is the result of a point mutation in exon 9 and completely abolishes enzymatic activity. These patients suffer from severe asthma. Results from further studies indicated that the variant allele thr198 was found to be highly associated with total IgE concentrations in an atopic population and with 'asthma' in an asthmatic population (Kruse et al., 2000, Am. J. Hum. Genet. 66:1522-1530). The variant allele val379 was found to be highly associated with 'specific sensitization' in the atopic population and with 'asthma' in the asthmatic population.

The full length cDNA clone has been isolated (see U.S. Pat. Nos. 5,981,252 and 5,968,818) and the DNA sequence has been determined. The complete amino acid sequence has been deduced from the DNA sequence. A gene encoding the human lipoprotein-associated phospholipase A2 polypeptide is located at gene map locus 6p21.2-p12.

OBJECTS OF THE INVENTION

Although cDNA encoding the above-disclosed protein, lipoprotein associated phospholipase A2, has been isolated (e.g. see accession no. AX006795 and NM_005084), its exact chromosome location en and exon/intron/regulatory organization have not been determined. Furthermore, genomic DNA encoding the polypeptide has not been isolated. Noncoding sequences play a significant role in regulating the expression of polypeptides as well as the processing of RNA encoding these polypeptides.

There is clearly a need for obtaining genomic polynucleotide sequences encoding the lipoprotein-associated phospholipase A2 polypeptide. Therefore, it is an object of the invention to isolate such genomic polynucleotide sequences.

There is also a need to develop means for identifying mutations, duplications, translocations, polysomies and mosaicism as may affect the lipoprotein associated phopholipase A2 gene.

SUMMARY OF THE INVENTION

The invention is directed to an isolated genomic polynucleotide, said polynucleotide obtainable from human genomic clone library RP11-446F17 having a nucleotide sequence at least 95% identical to a sequence selected from the group consisting of:
  (a) a polynucleotide encoding human lipoprotein-associated phospholipase A2 depicted in SEQ ID NO:1.
  (b) a polynucleotide consisting of SEQ ID NO:2, which encodes human lipoprotein-associated phospholipase A2 depicted in SEQ ID NO:1
  (c) a polynucleotide which is a variant of SEQ ID NO:2;
  (d) a polynucleotide which is an allelic variant of SEQ ID NO:2 ;
  (e) a polynucleotide which encodes a variant of SEQ ID NO:1;
  (f) a polynucleotide which hybridizes to any one of the polynucleotides specified in (a)-(e) and
  (g) a polynucleotide that is a reverse complement to the polynucleotides specified in (a)-(f) and
  (h) containing at least 10 transcription factor binding sites selected from the group consisting of AP1-C, AP1_Q4, AP4-Q5, DELTAEF1-01, GATA1__04, GATA1-06, GATA2-02, GATA3__02, GATA-C, LMO2COM-02, LYF1-01, MYOD_Q6, MZF__01, NFAT_Q6, NKX25-01, S8-01, SOX5-01, TATA-C, and TCF11-01
as well as nucleic acid constructs, expression vectors and host cells containing these polynucleotide sequences.

The polynucleotides of the present invention may be used to modulate human lipoprotein-associated phospholipase A2 levels in a subject in need thereof. Specifically, it may be used for the manufacture of a gene therapy for the prevention, treatment or amelioration of a medical condition such as asthma or systemic lupus erythematosus by adding an amount of a composition comprising said polynucleotide effective to prevent, treat or ameliorate said medical condition.

The invention is further directed to obtaining these polypeptides by
(a) culturing host cells comprising these sequences under conditions that provide for the expression of said polypeptide and
(b) recovering said expressed polypeptide.

The polypeptides obtained may be used to produce antibodies by
(a) optionally conjugating said polypeptide to a carrier protein;
(b) immunizing a host animal with said polypeptide or peptide-carrier protein conjugate of step (a) with an adjuvant and
(c) obtaining antibody from said immunized host animal.

The invention is further directed to polynucleotides that hybridize to noncoding regions of said polynucleotide sequences as well as antisense oligonucleotides to these polynucleotides as well as antisense mimetics. The polynucleotides, antisense oligonucleotides or mimetics may be used to modulate human lipoprotein-associated phospholipase A2 levels in a subject in need thereof and for the manufacture of a medicament for prevention, treatment or amelioration of a medical condition, such as atherosclerosis. The invention is further directed to kits comprising these polynucleotides and kits comprising these antisense oligonucleotides or mimetics.

In a specific embodiment, the noncoding regions are transcription regulatory regions. The transcription regulatory regions may be used to produce a heterologous peptide by expressing in a host cell, said transcription regulatory region operably linked to a polynucleotide encoding the heterologous polypeptide and recovering the expressed heterologous polypeptide.

The polynucleotides and antisense oligonucleotides of the present invention may be used to diagnose a pathological condition such as asthma in a subject comprising
(a) determining the presence or absence of a mutation in the polynucleotides of the present invention or fragments thereof and
(b) diagnosing a pathological condition or a susceptibility to a pathological condition based on the presence or absence of said mutation.

DETAILED DESCRIPTION OF THE INVENTION

The invention is directed to isolated genomic polynucleotide fragments that encode human lipoprotein-associated phospholipase A2, which in a specific embodiment is the human lipoprotein-associated phospholipase A2 gene, as well as vectors and hosts containing these fragments and polynucleotide fragments hybridizing to noncoding regions, as well as antisense oligonucleotides to these fragments.

As defined herein, a "gene" is the segment of DNA involved in producing a polypeptide chain; it includes regions preceding and following the coding region, as well as intervening sequences (introns) between individual coding segments (exons).

As defined herein "isolated" refers to material removed from its original environment and is thus altered "by the hand of man" from its natural state. An isolated polynucleotide can be part of a vector, a composition of matter or can be contained within a cell as long as the cell is not the original environment of the polynucleotide.

The polynucleotides of the present invention may be in the form of RNA or in the form of DNA, which DNA includes genomic DNA and synthetic DNA. The DNA may be double-stranded or single-stranded and if single stranded may be the coding strand or non-coding strand.

The polynucleotides of the invention have at least a 95% identity and may have a 96%, 97%, 98% or 99% identity to the polynucleotides depicted in SEQ ID NO:2 & 3 as well as the polynucleotides in reverse sense orientation, or the polynucleotide sequences encoding the human lipoprotein-associated phospholipase A2 polypeptide depicted in SEQ ID NO:1 A polynucleotide having 95% "identity" to a reference nucleotide sequence of the present invention, is identical to the reference sequence except that the polynucleotide sequence may include, on average, up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identify, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total numbers of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for purposes of the present invention.

A polypeptide that has an amino acid sequence at least, for example, 95% "identical" to a query amino acid sequence is identical to the query sequence except that the subject polypeptide sequence may include on average, up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the referenced sequence or in one or more contiguous groups within the reference sequence.

A preferred method for determining the best overall match between a query sequence (a sequence of the present invention) and a subject sequence, also referred to as a global sequence alignment, can be determined using the FASTDB computer program based on the algorithm of Brutlag et al. (Com. App. Biosci. (1990) 6:237-245). In a sequence alignment, the query and subject sequence are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

The invention also encompasses polynucleotides that hybridize to the polynucleotides depicted in SEQ ID NO: 2. A polynucleotide "hybridizes" to another polynucleotide, when a single-stranded form of the polynucleotide can anneal to the other polynucleotide under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a temperature of 42° C., can be used, e.g., 5×SSC, 0.1% SDS, 0.25% milk, and no formamide; or 40% formamide, 5×SSC, 0.5% SDS). Moderate stringency hybridization conditions correspond to a higher temperature of 55° C., e.g., 40% formamide, with 5× or 6×SCC. High stringency hybridization conditions correspond to the highest temperature of 65° C., e.g., 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA.

Polynucleotide and Polypeptide Variants

The invention is directed to both polynucleotide and polypeptide variants. A "variant" refers to a polynucleotide or polypeptide differing from the polynucleotide or polypeptide of the present invention, but retaining essential properties thereof. Generally, variants are overall closely similar and in many regions, identical to the polynucleotide or polypeptide of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred.

The invention also encompasses allelic variants of said polynucleotides. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the variant polypeptides may differ from the amino acid sequences depicted in SEQ ID NO:1 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

Noncoding Regions

The invention is further directed to polynucleotide fragments containing or hybridizing to noncoding regions of the human lipoprotein-associated phospholipase A2 gene. These include but are not limited to an intron, a 5'-non-coding region, a 3'-non-coding region and splice junctions (see Table 1), as well as transcription factor binding sites (see Table 2). The polynucleotide fragments may be a short polynucleotide fragment which is between about 8 nucleotides to about 40 nucleotides in length. Such shorter fragments may be useful for diagnostic purposes. Such short polynucleotide fragments are also preferred with respect to polynucleotides containing or hybridizing to polynucleotides containing splice junctions. Alternatively larger fragments, e.g., of about 50, 150, 500, 600 or about 2000 nucleotides in length may be used.

TABLE 1

Exon/Intron Regions of the Lipoprotein-Associated Phospholipase A2 Gene in SEQ ID NO:2 (42,611 base pairs, forward strand coding).

| Exon | Nucleotide no. | Peptide Amino Acid no. |
|---|---|---|
| 1 | 11967-12071 | 1-35 |
| 2 | 17761-17886 | 36-77 |
| 3 | 18333-18476 | 78-125 |
| 4 | 20307-20399 | 126-156 |
| 5 | 22522-22590 | 157-179 |
| 6 | 23240-23365 | 180-221 |
| 7 | 24203-24316 | 222-259 |
| 8 | 25443-25532 | 260-289 |
| 9 | 26698-26868 | 290-346 |
| 10 | 29558-29707 | 347-396 |
| 11 | 30164-30298 | 397-441 |
| Stop codon | 30299-30301 | |

TABLE 2

Transcription Factor Binding Sites on the Lipoprotein Realated Phospholipase A2 Gene.

| Transcription Factor | No. of Binding Sites |
|---|---|
| AP1_C | 14 |
| AP1_Q4 | 4 |
| AP4_Q5 | 4 |

TABLE 2-continued

Transcription Factor Binding Sites on the Lipoprotein Realated Phospholipase A2 Gene.

| Transcription Factor | No. of Binding Sites |
|---|---|
| DELTAEF1_01 | 5 |
| GATA1_04 | 7 |
| GATA1_06 | 8 |
| GATA2_02 | 5 |
| GATA3_02 | 4 |
| GATA_C | 7 |
| LMO2COM_02 | 4 |
| LYF1_01 | 9 |
| MYOD_Q6 | 9 |
| MZF1_01 | 14 |
| NFAT_Q6 | 10 |
| NKX25_01 | 16 |
| S8_01 | 7 |
| SOX5_01 | 2 |
| TATA_C | 7 |
| TCF11_01 | 46 |

In a specific embodiment, such noncoding sequences are expression control sequences. These include but are not limited to DNA regulatory sequences, such as promoters, enhancers, repressors, terminators, and the like, that provide for the regulation of expression of a coding sequence in a host cell. In eukaryotic cells, polyadenylation signals are also control sequences.

In a more specific embodiment of the invention, the expression control sequences may be operatively linked to a polynucleotide encoding a heterologous polypeptide. Such expression control sequences may be about 50-200 nucleotides in length and specifically about 50, 100, 200, 500, 600, 1000 or 2000 nucleotides in length. A transcriptional control sequence is "operatively linked" to a polynucleotide encoding a heterologous polypeptide sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the DNA sequence under the control of the expression control sequence and production of the desired product encoded by the polynucleotide sequence. If a gene that one desires to insert into a recombinant DNA molecule does not contain an appropriate start signal, such a start signal can be inserted upstream (5') of and in reading frame with the gene.

The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription or RNA processing (triple helix (see Lee et al., Nucl. Acids Res., 6:3073 (1979); Cooney et al, Science, 241:456 (1988); and Dervan et al., Science, 251: 1360 (1991)), thereby preventing transcription and the production of said polypeptides.

Expression of Polypeptides
Isolated Polynucleotide Sequences

The human lipoprotein related phospholipase A2 gene is situated in genomic clone AC008104; contigs 21 and 20 of gi 8072415, and these two contigs are joined by clone AL591242 contig 9 of gi 14018186. Genomic clone AC008104 is reported by GENBANK to be derived from chromosome 18, whereas genomic clone AL591242 is reported by Genbank to be derived from chromosome 6. However, both Genbank reports indicate that the genomic clones were prepared from clone library RP11-446F17 (Osoegawa et al., 2001, Genome Res. 11:483-96).

The human genomic clone RP11-446F17 sequences of the gi versions noted above (gi 8072415 and gi 14018186) have been discovered to contain the human lipoprotein related phospholipase A2 gene by Genscan analysis (Burge et al., 1997, J. Mol. Biol. 268:78-94), BLAST2 and TBLASTN analysis (Altschul et al., 1997, Nucl. Acids Res. 25:3389-3402), in which the clone sequences were compared to the human lipoprotein related phospholipase A2 cDNA sequences, accession numbers AX006795 and NM_005084.

The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) or long range PCR may be used. In a specific embodiment, 5'- or 3'-non-coding portions of the gene may be identified by methods including but are not limited to, filter probing, clone enrichment using specific probes and protocols similar or identical to 5'- and 3'-"RACE" protocols which are well known in the art. For instance, a method similar to 5'-RACE is available for generating the missing 5'-end of a desired full-length transcript. (Fromont-Racine et al., 1993, Nucl. Acids Res. 21:1683-1684).

Once the DNA fragments are generated, identification of the specific DNA fragment containing the desired human lipoprotein-associated phospholipase A2 gene may be accomplished in a number of ways. For example, if an amount of a portion of a human lipoprotein-associated phospholipase A2 gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a hybridizable probe having a nucleotide sequence corresponding to at least a 10, and preferably a 15, nucleotide fragment of the sequences depicted in SEQ ID NO:2. Preferably, a fragment is selected that is highly unique to the polynucleotides of the invention. Those DNA fragments with substantial homology to the probe will hybridize. As noted above, the greater the degree of homology, the more stringent hybridization conditions can be used. In one embodiment, low stringency hybridization conditions are used to identify a homologous human lipoprotein-associated phospholipase A2 polynucleotide. However, in a preferred aspect, a nucleic acid encoding a polypeptide of the invention will hybridize to a nucleic acid derived from the polynucleotide sequence depicted in SEQ ID NO:2 or hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the human lipoprotein-associated phospholipase A2 polypeptide.

A gene encoding human lipoprotein-associated phospholipase A2 polypeptide can also be identified by mRNA selection, i.e., by nucleic acid hybridization followed by in vitro translation. In this procedure, fragments are used to isolate complementary mRNAs by hybridization. Immunoprecipitation analysis or functional assays of the in vitro translation products of the products of the isolated mRNAs identifies the mRNA and, therefore, the complementary DNA fragments, that contain the desired sequences.

Nucleic Acid Constructs

The present invention also relates to nucleic acid constructs comprising a polynucleotide sequence containing the exon/intron segments of the human lipoprotein-associated phospholipase A2 gene operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The invention is further directed to a nucleic acid construct comprising expression control sequences derived from SEQ ID NO: 2 a heterologous polynucleotide sequence.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5'-end of the mRNA and a transcription terminator sequence located just downstream of the open reading frame at the 3'-end of the mRNA. A coding sequence can include, but is not limited to, DNA, cDNA, and recombinant nucleic acid sequences.

The isolated polynucleotide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequence may be an appropriate promoter sequence, a nucleic acid sequence which is recognized by a host cell for expression of the nucleic acid sequence. The promoter sequence contains transcriptional control sequences which regulate the expression of the polynucleotide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Komaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), NA2-tpi (a hybrid of the promoters from the genes encoding *Aspergillus niger* neutral alpha-amylase and *Aspergillus oryzae* triose phosphate isomerase), and mutant, truncated, and hybrid promoters thereof.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3'-terminus of the nucleic acid sequence encoding the polypeptide. Any terminator which is functional in the host cell of choice may be used in the present invention.

Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes encoding *Saccharomyces cerevisiae* enolase, *Saccharomyces cerevisiae* cytochrome C(CYC1), or *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5'-terminus of the nucleic acid sequence encoding the polypeptide. Any leader sequence that is functional in the host cell of choice may be used in the present invention.

Preferred leaders for filamentous fungal host cells are obtained from the genes encoding *Aspergillus oryzae* TAKA amylase and *Aspergillus nidulans* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

The control sequence may also be a polyadenylation sequence, a sequence which is operably linked to the 3'-terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region, which codes for an amino acid sequence linked to the amino terminus of the polypeptide which can direct the encoded polypeptide into the cell's secretory pathway. The 5'-end of the coding sequence of the nucleic acid sequence may inherently contain a signal peptide coding region naturally linked in translation reading frame with the segment of the coding region which encodes the secreted polypeptide. Alternatively, the 5'-end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed polypeptide into the secretory pathway of a host cell of choice may be used in the present invention.

An effective signal peptide coding region for bacterial host cells is the signal peptide coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), or the *Bacillus subtilis* prsA gene. Further signal peptides are described by Simonen and Palva, 1993, *Microbiological Reviews* 57: 109-137.

An effective signal peptide coding region for filamentous fungal host cells is the signal peptide coding region obtained from the *Aspergillus oryzae* TAKA amylase gene, *Aspergillus niger* neutral amylase gene, *Aspergillus niger* glucoamylase gene, *Rhizomucor miehei* aspartic proteinase gene, *Humicola lanuginosa* cellulase gene, or *Humicola lanuginosa* lipase gene.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the polynucleotide of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5Ō-phosphate decarboxylase), sC (sulfate adenyltransferase), trpC (anthranilate synthase), as well as equivalents from other species. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell genome or autonomous replication of the vector in the cell independent of the genome of the cell.

For integration into the host cell genome, the vector may rely on the polynucleotide sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional polynucleotide sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a polynucleotide sequence of the present invention may be inserted into the host cell to increase production of the gene product. An increase in the copy number of the polynucleotide sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus*, *Bacillus licheniformis*, *Bacillus stearothermophilus* or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian cell (e.g., human cell), an insect cell, a plant cell or a fungal cell. Mammalian host cells that could be used include but are not limited to human Hela, 293, H9 and Jurkat cells, mouse NIH3t3 and C127 cells, Cos 1, Cos 7 and CV1, quail QC1-3 cells, mouse L cells and Chinese Hamster ovary (CHO) cells. These cells may be transfected with a vector containing a transcriptional regulatory sequence, a protein coding sequence and transcriptional termination sequences. Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The host cell may be a fungal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). The fungal host cell may also be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980). The fungal host cell may also be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology*, Methods in Enzymology, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. In a specific embodiment, an enzyme assay may be used to determine the activity of the polypeptide. For example, human lipoprotein-associated phospholipase A2 can be assayed by its ability to release fatty acids from phospholipids. Caslake et al (Atherosclerosis 150: 413-19, 2000) have described a specific immunoassay for the enzyme.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Antibodies

According to the invention, the human lipoprotein-associated phospholipase A2 polypeptide produced according to the method of the present invention may be used as an immunogen to generate any of these antibodies. Such antibodies include but are not limited to polyclonal, monoclonal, chimeric, single chain, Fab fragments, and an Fab expression library.

Various procedures known in the art may be used for the production of antibodies. For the production of antibody, various host animals can be immunized by injection with the polypeptide thereof, including but not limited to rabbits, mice, rats, sheep, goats, etc. In one embodiment, the polypeptide or fragment thereof can optionally be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the human lipoprotein-associated phospholipase A2 polypeptide, any technique that provides for the production of antibody molecules by continuous cell lines in culture may be used. These include but are not limited to the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, J. Bacteriol. 159-870; Neuberger et al., 1984, Nature 312:604-608; Takeda et al., 1985, Nature 314:452-454) by splicing the genes from a mouse antibody molecule specific for the human lipoprotein-associated phospholipase A2 polypeptide together with genes from a human antibody molecule of appropriate biological activity can be used; such antibodies are within the scope of this invention.

According to the invention, techniques described for the production of single chain antibodies (U.S. Pat. No. 4,946,778) can be adapted to produce polypeptide-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for the human lipoprotein-associated phospholipase A2 polypeptide.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a particular polypeptide, one may assay generated hybridomas for a product which binds to a particular polypeptide fragment containing such epitope. For selection of an antibody specific to a particular polypeptide from a particular species of animal, one can select on the basis of positive binding with the polypeptide expressed by or isolated from cells of that species of animal.

Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Uses of Polynucleotides
Diagnostics

Polynucleotides containing noncoding regions of SEQ ID NO:2 may be used as probes for detecting mutations from samples from a patient. Genomic DNA may be isolated from the patient. A mutation(s) may be detected by Southern blot analysis, specifically by hybridizing restriction digested genomic DNA to various probes and subjecting to agarose electrophoresis. Alternatively, these polynucleotides may be used as PCR primers and be used to amplify the genomic DNA isolated from the patients. Additionally, primers may be obtained by routine or long range PCR that yield products containing contiguous intron/exon sequence and products containing more than one exon with intervening intron. The sequence of the amplified genomic DNA from the patient may be determined using methods known in the art. Such probes may be between 10-100 nucleotides in length and may preferably be between 20-50 nucleotides in length.

Thus the invention is thus directed to kits comprising these polynucleotide probes. In a specific embodiment, these probes are labeled with a detectable substance.

Antisense Oligonucleotides and Mimetics

The antisense oligonucleotides or mimetics of the present invention may be used to decrease levels of a polypeptide. For example, human lipoprotein-associated phospholipase A2 has been found to be associated with atherosclerosis and diabetes. Therefore, the human lipoprotein-associated phospholipase A2 antisense oligonucleotides of the present invention could be used to inhibit progression of atherosclerosis, including coronary artery disease.

The antisense oligonucleotides of the present invention may be formulated into pharmaceutical compositions. These compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ as found to be effective in in vitro and in vivo animal models.

In general, dosage is from 0.01 ug to 10 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 10 g per kg of body weight, once or more daily, to once every 20 years.

Gene Therapy

Human lipoprotein-associated phospholipase A2 deficiency states have been described (Yamada et al., Metabolism 47: 177-81, 1998). Therefore, the human lipoprotein-associated phospholipase A2 gene may be used to via gene therapy to correct any such deficiency state or disorders associated with such deficiency states (e.g., asthma).

As described herein, the polynucleotide of the present invention may be introduced into a patient's cells for therapeutic uses. As will be discussed in further detail below, cells can be transfected using any appropriate means, including viral vectors, as shown by the example, chemical transfectants, or physico-mechanical methods such as electroporation and direct diffusion of DNA. See, for example, Wolff, Jon A, et al., "Direct gene transfer into mouse muscle in vivo," Science, 247, 1465-1468, 1990; and Wolff, Jon A, "Human dystrophin expression in mdx mice after intramuscular injection of DNA constructs," Nature, 352, 815-818, 1991. As used herein, vectors are agents that transport the gene into the cell without degradation and include a promoter yielding expression of the gene in the cells into which it is delivered. As will be discussed in further detail below, promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes:

a) Biological agents derived from viral, bacterial or other sources.

b) Chemical physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells. Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression. Polynucleotides are inserted into vector genomes using methods well known in the art.

Retroviral vectors are the vectors most commonly used in clinical trials, since they carry a larger genetic payload than other viral vectors. However, they are not useful in non-proliferating cells. Adenovirus vectors are relatively stable and easy to work with, have high titers, and can be delivered in aerosol formulation. Pox viral vectors are large and have several sites for inserting genes, they are thermostable and can be stored at room temperature.

Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1 a promoter or the Ad2 major late promoter (MLP). Similarly, those of ordinary skill in the art can construct adenoviral vectors utilizing endogenous or heterologous poly A addition signals.

Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN and LIPOFECTACE, which are formed of cationic lipids such as N-[1-(2,3 dioleyloxy)-propyl]-n,n,n-trimethylammonium chloride (DOTMA) and dimethyl dioctadecylammonium bromide (DDAB). Numerous methods are also published for making liposomes, known to those skilled in the art.

For example, Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold, Nature 337:387 (1989)). Intravenous injection of cationic lipid-plasmid complexes into mice has been shown to result in expression of the DNA in lung (Brigham et al., Am. J. Med. Sci. 298:278 (1989)). See also, Osaka et al., J. Pharm. Sci. 85(6):612-618 (1996); San et al., Human Gene Therapy 4:781-788 (1993); Senior et al., Biochemica et Biophysica Acta 1070:173-179 (1991); Kabanov and Kabanov, Bioconjugate Chem. 6:7-20 (1995); Remy et al., Bioconjugate Chem. 5:647-654 (1994); Behr, J-P., Bioconjugate Chem 5:382-389 (1994); Behr et al., Proc. Natl. Acad. Sci., USA 86:6982-6986 (1989); and Wyman et al., Biochem. 36:3008-3017 (1997).

Cationic lipids are known to those of ordinary skill in the art. Representative cationic lipids include those disclosed, for example, in U.S. Pat. No. 5,283,185; and e.g., U.S. Pat. No. 5,767,099. In a preferred embodiment, the cationic lipid is $N^{4}$-spermine cholesteryl carbamate (GL-67) disclosed in U.S. Pat. No. 5,767,099. Additional preferred lipids include N4 spermidine cholestryl carbamate (GL-53) and 1-(N4-spermind)-2,3-dilaurylglycerol carbamate (GL-89).

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule.

Invention vectors may be delivered to the target cells in a suitable composition, either alone, or complexed, as provided above, comprising the vector and a suitably acceptable carrier. The vector may be delivered to target cells by methods known in the art, for example, intravenous, intramuscular, intranasal, subcutaneous, intubation, lavage, and the like. The vectors may be delivered via in vivo or ex vivo applications. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

In a specific embodiment, the vector is transfected into antigen-presenting cells. Suitable sources of antigen-presenting cells (APCs) include, but are not limited to, whole cells such as dendritic cells or macrophages; purified MHC class I molecule complexed to beta2-microglobulin and foster antigen-presenting cells. In a specific embodiment, the vectors of the present invention may be introduced into T cells or B cells using methods known in the art (see, for example, Tsokos and Nepom, 2000, J. Clin. Invest. 106:181-183).

The invention described and claimed herein is not to be limited in scope by the specific embodiments herein disclosed, since these embodiments are intended as illustrations of several aspects of the invention. Any equivalent embodi ments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosure of which are incorporated by reference in their entireties.

What is claimed is:

1. A method of detecting the presence or absence of a polynucleotide in a sample, said polynucleotide selected from the group consisting of: (i) a polynucleotide which is at least 99% identical to the polynucleotide of SEQ ID NO:2, which encodes a polypeptide which is at least 99% identical to the amino acid sequence of SEQ ID NO:1, wherein said polypeptide has human lipoprotein-associated phospholipase A2 activity; (ii) a fragment of (i) comprising at least nucleotides 11967-30301, which encodes a polypeptide which is at least 99% identical to the amino acid sequence of SEQ ID NO:1, wherein said polypeptide has lipoprotein-associated phospholipase A2 activity; and (c) the full complement of (i) or (ii), said method comprising
   (a) contacting the sample with an isolated polynucleotide probe or primer, wherein said probe or primer is a fragment of a polynucleotide which is at least 99% identical to SEQ ID NO:2 and wherein said polynucleotide probe or primer comprises at least 20 contiguous nucleotides of SEQ ID NO:2 or its full complement which contains a transcription factor binding site at an NFAT_Q6 site at nucleotides 11523-11541, and
   (b) determining whether the polynucleotide probe or primer binds to a polynucleotide sequence in the sample, wherein binding of a polynucleotide of the sample to said probe or primer in step (a) detects the presence of a polynucleotide comprising SEQ ID NO:2.

2. The method according to claim 1, wherein said sample is contacted with a probe between 50-2000 contiguous nucleotides in length.

3. A method for detecting the presence of a polynucleotide in a sample, said polynucleotide selected from the group consisting of: (i) a polynucleotide which is at least 99% identical to the polynucleotide of SEQ ID NO:2; (ii) a fragment of (i) comprising at least nucleotides 11967-30301 of SEQ ID NO:2, and (iii) the full complement of (i) or (ii) in a sample, comprising
   (a) contacting the sample with a polynucleotide probe or primer comprising the 5'-noncoding region, 3'-noncoding region or intron region of SEQ ID NO:2 or its complementary sequence and (b) determining whether the polynucleotide probe or primer binds to said nucleic acid molecule in the sample.

4. The method according to claim 3, wherein the polynucleotide or probe comprises the intron region of SEQ ID NO:2 or its complementary sequence.

5. The method according to claim 1, wherein the polynucleotide or probe is a DNA or RNA sequence.

6. The method according to claim 3, wherein the polynucleotide or probe is a DNA or RNA sequence.

* * * * *